(12) United States Patent
Strommer et al.

(10) Patent No.: US 6,233,476 B1
(45) Date of Patent: May 15, 2001

(54) MEDICAL POSITIONING SYSTEM

(75) Inventors: Gera M Strommer; Uzi Eichler, both of Haifa (IL)

(73) Assignee: Mediguide Ltd., Haifa (IL)

(*) Notice: Subject to any disclaimer, the term of this patent is extended or adjusted under 35 U.S.C. 154(b) by 0 days.

(21) Appl. No.: 09/314,474

(22) Filed: May 18, 1999

(51) Int. Cl.[7] .................................................. A61B 5/05
(52) U.S. Cl. ............................................................ 600/424
(58) Field of Search .................................. 600/424, 410, 600/409, 411, 437, 439, 462, 461, 463, 407, 109, 112, 114, 118; 128/916

(56) References Cited

U.S. PATENT DOCUMENTS

| | | | |
|---|---|---|---|
| 4,794,931 | * 1/1989 | Yock | 128/660.03 |
| 5,318,025 | * 6/1994 | Dumoulin et al. | 128/653.2 |
| 5,646,525 | 7/1997 | Gilboa | 324/207.17 |
| 5,704,361 | * 1/1998 | Seward et al. | 128/662.06 |
| 5,729,129 | 3/1998 | Acker | 324/207.12 |
| 5,752,513 | 5/1998 | Acker et al. | 128/653.1 |
| 5,833,608 | * 11/1998 | Acker | 600/409 |
| 5,840,025 | 11/1998 | Ben-Haim | 600/424 |
| 5,899,860 | * 5/1999 | Pfeiffer et al. | 600/424 |
| 5,921,934 | * 7/1999 | Teo | 600/468 |

OTHER PUBLICATIONS

Stephen B. Soloman, Peter White Jr., David E. Acker, John Strandberg, Anthony C. Venbrux Real–time Bronchoscope Tip Localization Enables Three–dimensional CT Image Guidance for Transbronchial Needle Aspiration in Swine. CHEST; The Cardiopulmonary and Critical Care Journal, Nov. 1998, vol. 114/5, pp. 1405–1410. The American College of Chest Physicians, U.S.A.

* cited by examiner

*Primary Examiner*—Marvin M. Lateef
*Assistant Examiner*—Eleni Mantis Mercader
(74) *Attorney, Agent, or Firm*—Darby & Darby

(57) ABSTRACT

Medial device comprising a housing, a magnetic detection probe, for detecting a plurality of magnetic fields, a biometric unit and a controller, connected to said magnetic detection probe, said biometric unit and said storage unit, wherein said controller receives magnetic field detection information from said magnetic detection probe, and wherein said controller operates said biometric unit in association with said magnetic field detection information.

47 Claims, 17 Drawing Sheets

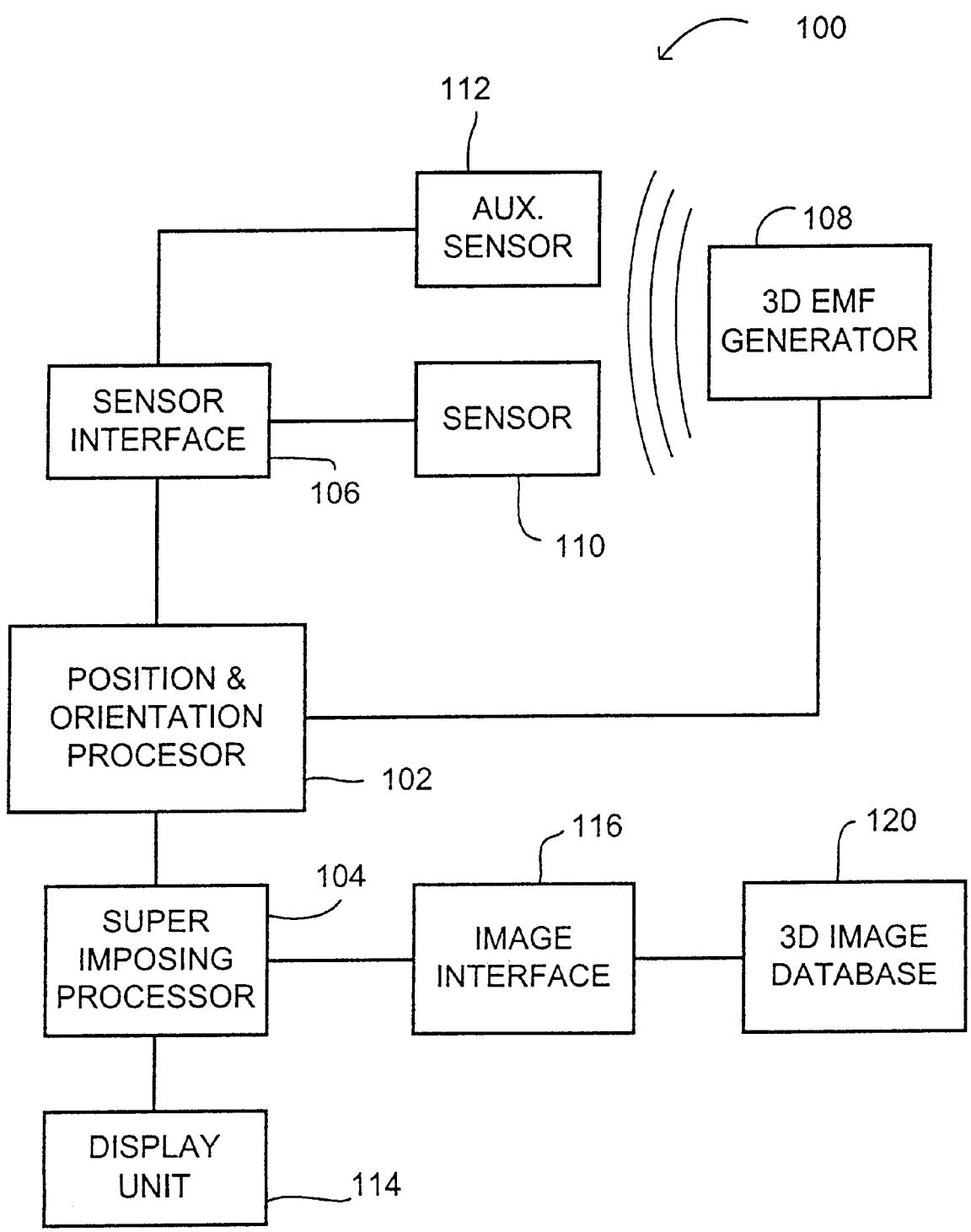

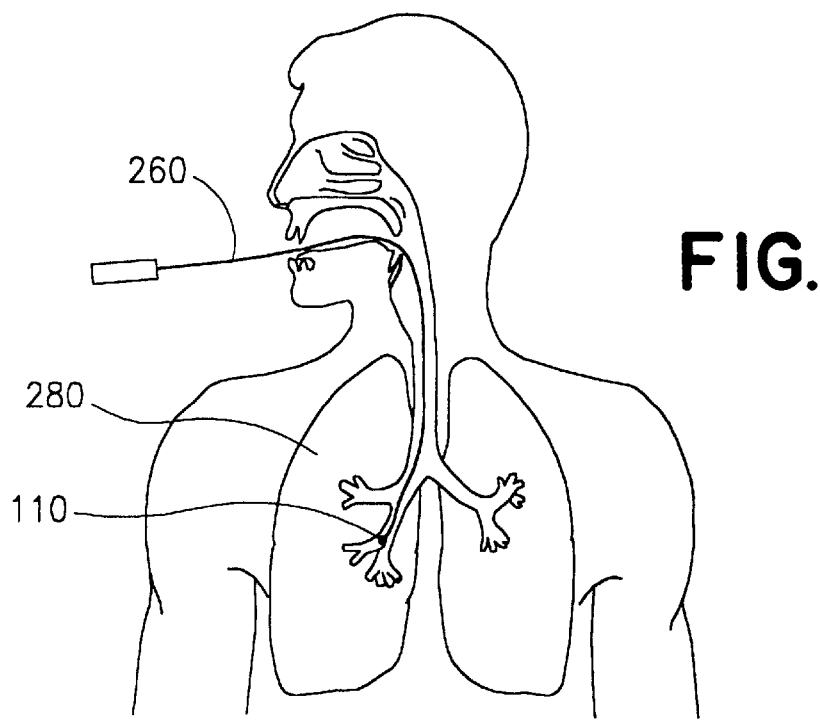
FIG. 3A
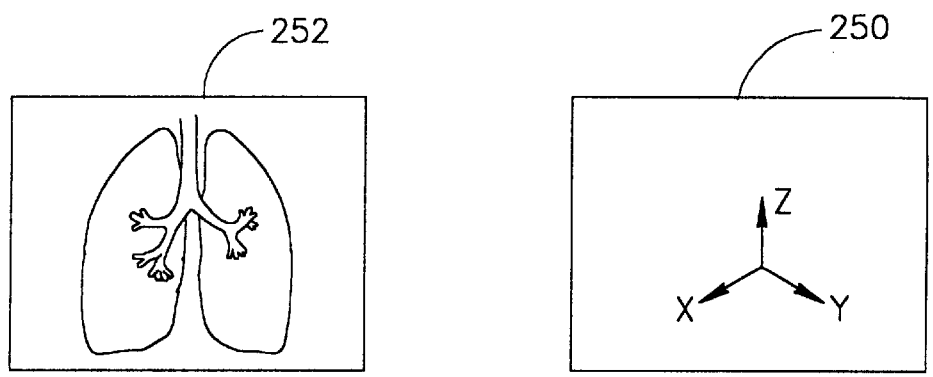
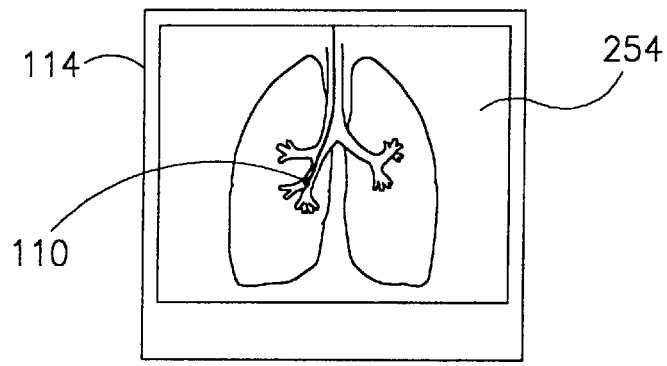
FIG. 3B

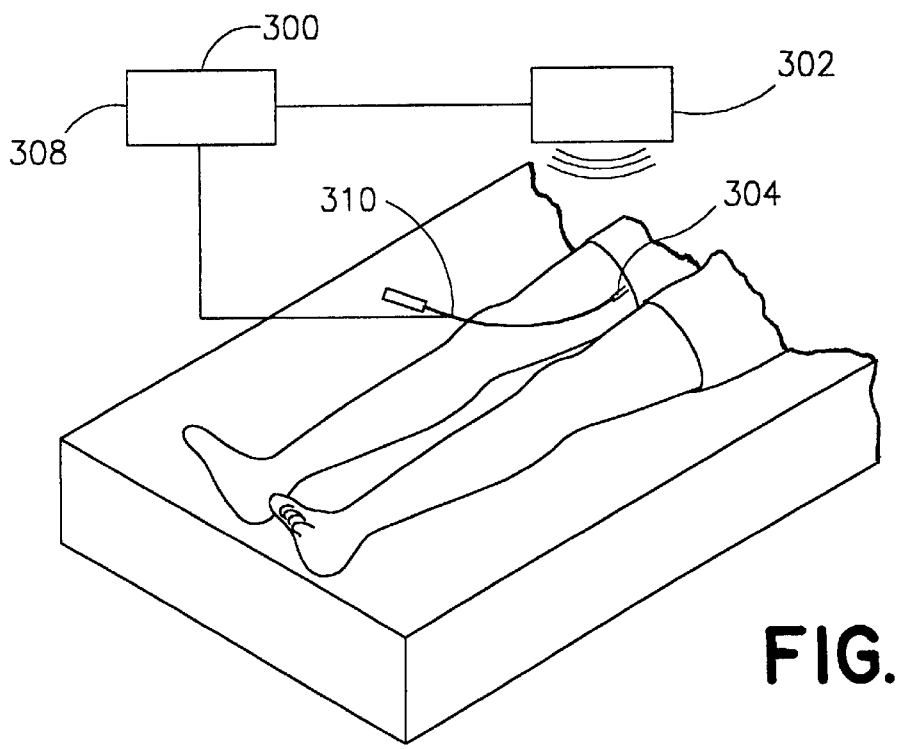
FIG. 4A
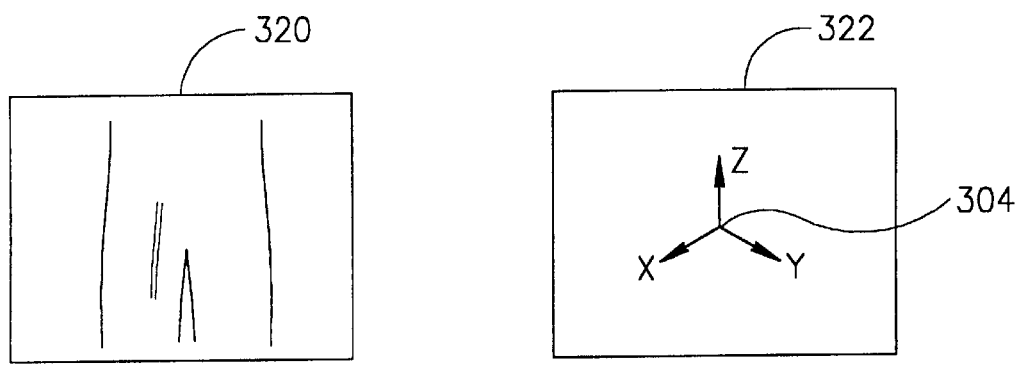
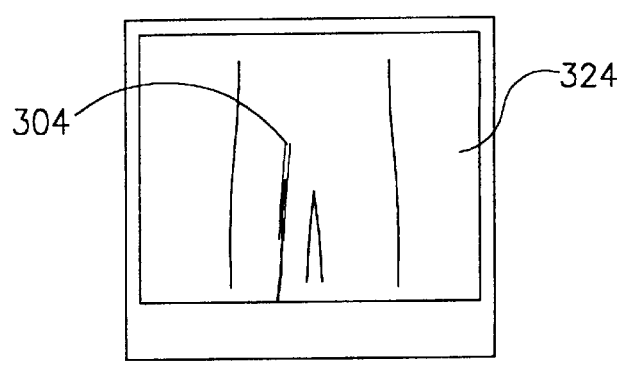
FIG. 4B

MEDICAL POSITIONING SYSTEM

FIELD OF THE INVENTION

The present invention relates to positioning systems in general, and to methods and systems for positioning an item within a living tissue, in particular.

BACKGROUND OF THE INVENTION

Minimal Invasive Endoscopic Surgery (MIES) provides the means by which less invasive medical procedures can be employed cost-effectively for a huge segment of the patient population, covering the most important medical specialties and surgical interventions. While patients benefit from this innovative technique, much of the credit for its success must be given to physicians/endoscopists and to manufacturers who created the endoscopic video imaging systems and unique procedure-specific devices, which together made millions of procedures possible each year since the technique gained prominence in the late 1980's.

MIES reduces the cost of the overall procedure by reducing the number of days that a patient spends in a medical facility and by significantly reducing the trauma which is inflicted on the patient, which reduces the chance for complication during a procedure and afterwards.

Systems for determining the location of a medical device within a treated living tissue are known in the art. In general, these systems are divided into two major groups, which are visual systems, semi visual systems and non-visual positioning system.

A conventional visual system includes an optical imaging element such as a fiber optic based device. The imaging element is inserted into the body of the patient and assists the physician in locating any surgical tool therein. One such system is called an endoscope. A conventional endoscope includes a dilating catheter in which lighting means, visual image unit and a surgical tool, are inserted.

Semi-visual systems often include a real time imaging device such as an ultrasound mechanism, which is combined with the tip of the endoscope. An example for such a system is the EUB-525 ultrasound system with the 10R probe, manufactured and sold by Hitachi.

Non visual systems include additional means, which assist the user in determining the location of the medical device within the body of the patient. U.S. Pat. No. 5,729, 129 to Acker is directed to a magnetic location system with feedback adjustment of magnetic field generator. It is noted that this system is subjected to metal object interference, which is produced by various metal objects, located in the vicinity of the system. Another disadvantage of this system is that the general method of operation of such a system includes three consecutive steps: transmitting an electromagnetic signal; detecting this signal and adjusting the electromagnetic signal according to the detected one. Hence the refresh rate of this system is significantly slow.

U.S. Pat. No. 5,840,025 to Ben-Haim, is directed to an Apparatus And Method for Treating Cardiac Arrhythmias. According to Ben-Haim, a catheter is inserted into the body of the patient and located in selected locations within the heart. The tip of the catheter includes a transmitting antenna, which transmits an electromagnetic signal. This signal is detected by external antennas and is then used to determine the location of the tip of the catheter. Finally, this information is super imposed on a pre-acquired image of the treated area.

U.S. Pat. No. 5,752,513 to Acker et al is directed to a Method And Apparatus for Determining the Position of an Object. The system uses an electromagnetic transmitter and receiver arrangement to determine the location and orientation of a medical device, which is inserted in the body of a patient. The location and orientation information is incorporated with a pre-acquired image of the treated area, using a plurality of markers, which have both visual as well as magnetic characteristics. It is noted that the accuracy of this apparatus significantly decreases in the presence of metal objects, which deform the magnetic fields.

A Bronchoscope is a specific type of an endoscope, which is directed for treating lungs. During a conventional lung treatment, the physician inserts the bronchoscope into the lung of the patient and operates the surgical tool (which can be a clamp, a brush, a laser device and the like) while viewing the inside volume of the lung, using the visual image unit.

It will be appreciated by those skilled in the art that the width of the bronchoscope is significant. Hence, a bronchoscope can not be used to treat places, where the access thereto is narrower than the diameter of the bronchoscope. In the case of lung treatment, the conventional method is to place the patient on an X-ray table system and place an X-ray video camera on top, which provides continuous images of the treated area and the surgical tool inserted therein. It will be appreciated by those skilled in the art that this method suffers several disadvantages. The imaging resolution is often not high enough and provides only vague indication of the location of the surgical too. Operating an X-ray table requires a medical staff of several people. X-ray based technology is known in the art as inflicting considerable hazards on the medical staff operating it.

Gastroscopy is also known in the art. One type of gastroscopes includes an ultrasound transceiver at the tip end, providing continuous semi-visual information, enabling the physician to operate a surgical tool using this information. It will be appreciated by those skilled in the art that operating an ultrasound-visualizing device requires a considerable training period, which conventionally is in the order of 18–24 months. Such a combined ultrasound gastroscopy system is the FG-34UX model, manufactured and soled by Pentax.

Another type of positioning system includes the UltraGuide 1000, which is a combined ultrasound and magnetic location system. This system includes an external ultrasound transducer and a magnetic field based location detection system, which is mounted on a firm surgical tool, such as a large needle. This ultrasound device enables the user to select an insertion point and angle that permit access, with a long needle, to a target within the body of the patient.

SUMMARY OF THE PRESENT INVENTION

It is an object of the present invention to provide a novel method and system for determining the location and orientation of objects, within a scanning volume, which overcomes the disadvantages of the prior art. It is another object of the present invention to provide a novel method and system for initiating and calibrating the location and orientation of a detector of the system, within the scanned volume.

It is a further object of the present invention to provide a novel method and system for obtaining an inner body three-dimensional image from a plurality of two dimensional images.

It is yet another object of the present invention to provide a novel method and system to operate within the body of the patient, wirelessly.

In accordance with the present invention, there is thus provided an apparatus for determining the position and orientation of a surgical tool relative to a reference frame, in association with an image. The apparatus includes a magnetic field transmitter, a detection probe, a signal generation module, connected to the magnetic field transmitter, a detection processor, connected to the detection probe and mounting means, for mounting onto the surgical tool.

The magnetic field transmitter, includes at least one magnetic field generating element. The detection probe includes at least one magnetic field detector The combined number of the magnetic fields generators and the magnetic field detectors is at least four. The signal generation module determines a transmit signal and provides the transmit signal to the magnetic field transmitter. The detection processor receives a detected signal from the detection probe, determines the location and orientation of the detection probe from the detected signal and indicates the location of the surgical tool within the image. The detection probe can include any number of magnetic field detectors.

The signal generation module can include a digital to analog converter and a signal processor connected thereto. The signal processor determines a digital transmit signal. The digital to analog converter converts the digital signal to a respective analog signal and provides the analog signal to the magnetic field transmitter. The digital signal can include any number of transmission channels. Each of the channels can include any number of frequencies.

In accordance with one aspect of the invention, each of the channels includes a plurality of frequencies.

In accordance with another aspect of the invention, the apparatus can further include an ultra-sound interface, for connecting to an ultrasound system capturing ultrasound frames. The detection processor constructs the image from the ultrasound frames, with respect to the detected location and orientation of the surgical tool It is noted that the detection probe can be wirelessly connected to the detection processor. The frequencies and for that matter the channels themselves, can either be transmitted in accordance with a predetermined non overlapping sequence or simultaneously In accordance with another aspect of the invention, there is provided a medial device which includes a housing, a magnetic detection probe, a biometric unit and a controller, connected to the magnetic detection probe, to the biometric unit and to the storage unit. The controller receives magnetic field detection information from the magnetic detection probe. The controller operates the biometric unit in association with the magnetic field detection information. It is noted that the housing can be shaped like a capsule.

The medial device can further include a transmitter, which is connected to the controller, for transmitting the magnetic field detection information. The biometric unit includes at least one of the devices in the list consisting of an image detection unit, a substance releasing unit and a biometric sampling unit. The medial device can further include a storage unit for storing the magnetic field detection information, connected to the controller.

The biometric unit can include a biomedical sensor, wherein the biometric unit provides detected biometric information to the controller and wherein the controller produces a plurality of records. Each of the records can thus include a portion of the biometric information and a respective portion of the detected magnetic field information. The controller can store the records in the storage unit.

The medial device can further include a wireless transmitter, connected to the controller, wherein the controller provides the records to the wireless transmitter and wherein the transmitter transmits the records to an external receiver. It is noted that the magnetic fields, which are detected by the medical device are generated by an external transmitter. These electromagnetic fields can be generated in accordance with either a predetermined non overlapping sequence, semi overlapping sequence or simultaneously and continuously.

In accordance with another aspect of the invention, there is provided a method for calibrating a reference image onto a volume, from which the image is produced. The method includes the steps of determining a plurality of locations in the volume, the locations being visible, and present in the reference image, detecting a magnetic field reading in each of the locations, and calibrating the reference image with respect to the magnetic field readings, onto the volume. This method eliminates the need to place special markers, which can be located either in the image or by a detector.

The method can further include the steps of receiving additional magnetic field readings, each in an additional location within the volume, and determining the location and orientation of the additional location, within the reference frame.

In accordance with yet a further aspect of the invention, there is thus provided an Imaging system which includes an inner body ultrasound detector, and a location and orientation detector, firmly attached to the inner body ultrasound detector. The inner body ultrasound detector detects a plurality of two-dimensional images and the location and orientation detector detects the location and orientation of each of the two-dimensional images. The system can further include a three dimensional image generator, connected to the inner body ultrasound detector and to the location and orientation detector. The three dimensional image generator processes the two-dimensional images, each with its respecting location and orientation information, thereby producing a three dimensional image.

The imaging system can include a storage unit, connected between the three dimensional image generator the inner body ultrasound detector and the location and orientation detector, for intermediately storing the two-dimensional images, each with its respecting location and orientation information.

The imaging system can further include a combining processor, connected to the three dimensional generator and interfacing at least one additional location and orientation detector. The combining processor receives additional location and orientation information from the additional location and orientation detectors. The combining processor produces an indication of the additional location and orientation information onto the three-dimensional image. The inner body ultrasound detector can include either an angular ultrasound transceiver or a radial ultrasound transceiver.

The location and orientation detector can include at least one axial magnetic detector. Each of the location and orientation detectors can detect magnetic field in at least one axial magnetic direction. The location and orientation detector can detect magnetic field in at least one frequency in each of the axial magnetic directions. The location and orientation detector is generally mounted on the inner body ultrasound detector.

The inner body ultrasound detector can be mounted on a catheter. In this case the location and orientation detector can be mounted on the tip of the catheter, in the vicinity of the inner body ultrasound detector.

In accordance with yet another aspect of the invention, there is provided a method for producing a three dimensional image, which includes the step of detecting a plurality of two-dimensional ultrasound images, from the inner section of a scanned volume. The method can further include the steps of detecting the location and orientation of a selected vector in each of the two dimensional ultrasound images, and determining a three dimensional representation for each of the two-dimensional images, according to the location and orientation thereof.

The method can further include the step of producing a three-dimensional image from the three-dimensional representations.

The method can further include the step of receiving additional location and orientation information and producing an indication thereof onto the three-dimensional image.

The method can further include the step of producing a visible representation of the three-dimensional image and the indication.

The method can further include the step of inserting an ultrasound detector into the inner section of the scanned volume. According to one aspect of the invention, the two-dimensional ultrasound images can include angular two-dimensional ultrasound images.

BRIEF DESCRIPTION OF THE DRAWINGS

The present invention will be understood and appreciated more fully from the following detailed description taken in conjunction with the drawings in which:

FIG. 1A is a schematic illustration of a location and orientation determination system, constructed and operative in accordance with a preferred embodiment of the present invention;

FIGS. 3A, 3B and 3C are illustrations of the location and orientation determination system of FIG. 1A, incorporated within a bronchoscope, constructed and operative in accordance with a further preferred embodiment of the present invention;

FIG. 4A is an illustration of a patient, a catheter and a location and orientation detection system, constructed and operative in accordance with another preferred embodiment of the present invention;

FIG. 4B is an illustration of the superimposing of the location information provided by the location and orientation detection system of FIG. 4A and a three dimensional image of a treated portion of the body of the patient;

DETAILED DESCRIPTION OF PREFERRED EMBODIMENTS

Figure 1B:
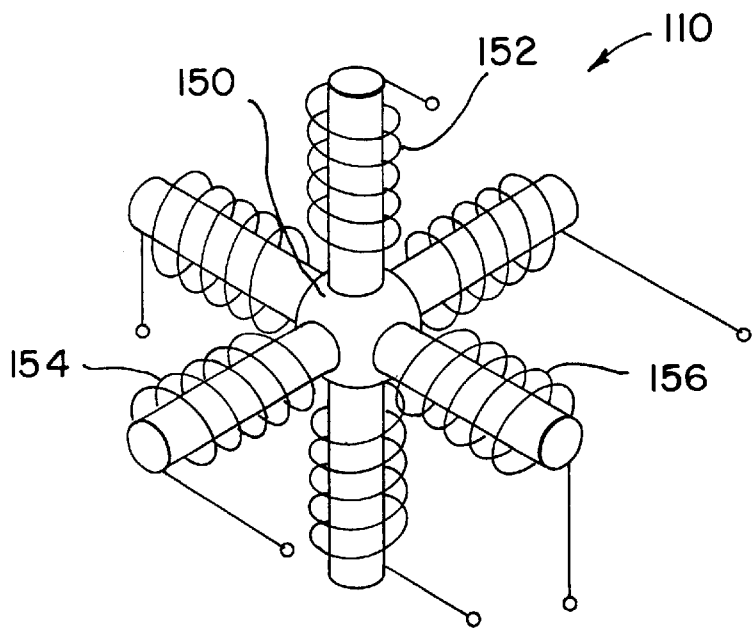
FIG. 1B is an illustration in detail of the sensor of the system of FIG. 1A.

The present invention overcomes the disadvantages of the prior art by providing a novel method and a novel system which provide accurate and harmless positioning of a medical device within a living tissue.

Reference is now made to FIG. 1A, which is a schematic illustration of a system, generally referenced 100, constructed and operative in accordance with a preferred embodiment of the present invention.

System 100 includes a position & orientation processor 102, a super imposing processor 104, a sensor interface 106, a main sensor 110, an auxiliary sensor 112, a 3D electromagnetic field generator 108, an image interface 116, a 3D image database 120 and a display unit 114. It is noted that system 100 can include additional 3D electromagnetic field generators.

The position & orientation processor 102 is connected to the 3D electromagnetic field generator 108, to the super imposing processor 104 and to the sensor interface 106. The image interface is connected to the 3D-image database 120 and to the super imposing processor 104. The super imposing processor 104 is further connected to the display unit 114. The sensor interface is further connected to the main sensor 110 and to the auxiliary sensor 112.

The 3D electromagnetic field generator 108 includes a plurality of electromagnetic generating elements such as coils, which produce a plurality of electromagnetic fields in a plurality of directions and in a plurality of magnitudes. It is noted that these fields can either be fixed or alternating. These fields are detected by each of the sensors 110 and 112. The electromagnetic field detection results, provide an indication of the location and orientation of the main sensor 110.

The main sensor 110 of system 110 is generally located on a probe or a medical tool, which is inserted within the inspected tissue. Auxiliary sensor 112 is generally located in the vicinity of the inspected tissue. It is noted that the use of such an auxiliary sensor enhances the performance of system 100 but is not essential. It is noted that more auxiliary sensors can be added to the system. For example, an auxiliary sensor can be attached to the body of the patient, providing reference to his movement.

The sensors 110 and 112 provide information related to detected electromagnetic fields, to the position and orientation processor 102. From this information and with respect to the fields generated by the 3D electromagnetic field generator 108, the position and orientation processor 102 determines the location and orientation of the sensor 110 and of auxiliary sensor 112. The position and orientation processor 102 produces respective location and orientation data, and provides it to the super imposing processor 104. It is noted that a system according to the present invention, can include a plurality of electromagnetic generators, such as the 3D electromagnetic field generator 108.

The 3D-image database 120 includes a pre-detected image of the inspected tissue and provides it to the super imposing processor 104. It is noted that the pre-detected image can be provided from any 3D image generating device, such as an X-ray detection system, a magnetic resonance imaging (MRI) system, an ultrasound imaging system and the like.

The 3D-image database 120 provides 3D image data to the super imposing processor 104, via the image interface 116. The super imposing processor 104 processes the location and orientation data, received from the location and orientation processor 102, with the 3D image data, received from the 3D image database. The super imposing processor 104 thereby produces an image, which includes a representation of the pre-detected 3D image, and an indication of the position and orientation of the sensor 110, thereon. The super imposing processor 104 provides this representation to the display unit 114, which in turn produces a respective image.

Figure 1C:
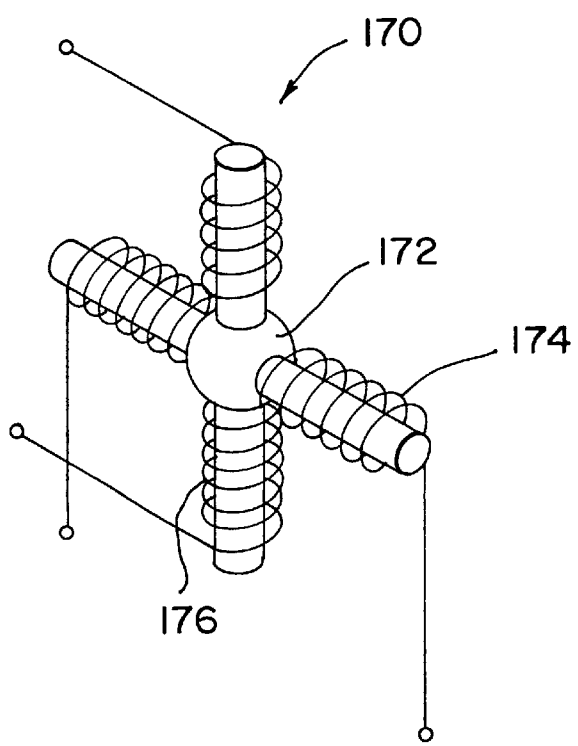
FIG. 1C is an illustration of a sensor, constructed and operative in accordance with a further preferred embodiment of the present invention.

Reference is further made to FIGS. 1B and 1C. FIG. 1B is an illustration of sensor 110 of system 100 of FIG. 1A. FIG. 1C is an illustration of a sensor, generally referenced 170, constructed and operative in accordance with a further preferred embodiment of the present invention.

Sensor 110 includes a core 150 and three coils 152, 154 and 156. It is noted that core 150 can be ferromagnetic. Each of the coils detects an electromagnetic field in a different direction. Hence, sensor 110 provides information with respect to three dimensions (x,y,z). It is noted that the core 150 can be replaced by other known means for amplifying the detected signal, such as using higher gain coils and the like. It is noted that any type of electromagnetic field sensors, such as Hall effect sensors, and the like, which is known in the art, is applicable for the present invention. Furthermore it is noted that the sensor can be used without a ferromagnetic core.

With reference to FIG. 1C, sensor 170 includes a core 172 and two coils 174 and 176. It is noted that core 172 can be ferromagnetic. Each of these coils 174 and 176 detects electromagnetic field in a different direction. Hence, sensor 170 provides information with respect to two dimensions, for example (x,y).

A location and orientation detection system for helmets, which operates according to the same principle is disclosed in U.S. Pat. Nos. 5,646,524 and 5,646,525, which are hereby incorporated by reference. The present invention utilizes such a system to determine the location and the orientation of invasive medical devices within a living tissue.

In accordance with a further aspect of the invention, each of the magnetic fields is generated using a plurality of frequencies. This novel aspect of the invention overcomes several disadvantages of the prior art, such as increasing the metal effect and the like. By taking into account the field measurements of a plurality of detected electromagnetic fields, the system of the invention, eliminates the disturbing effects of metal objects which may disrupt these electromagnetic fields.

Figure 6:
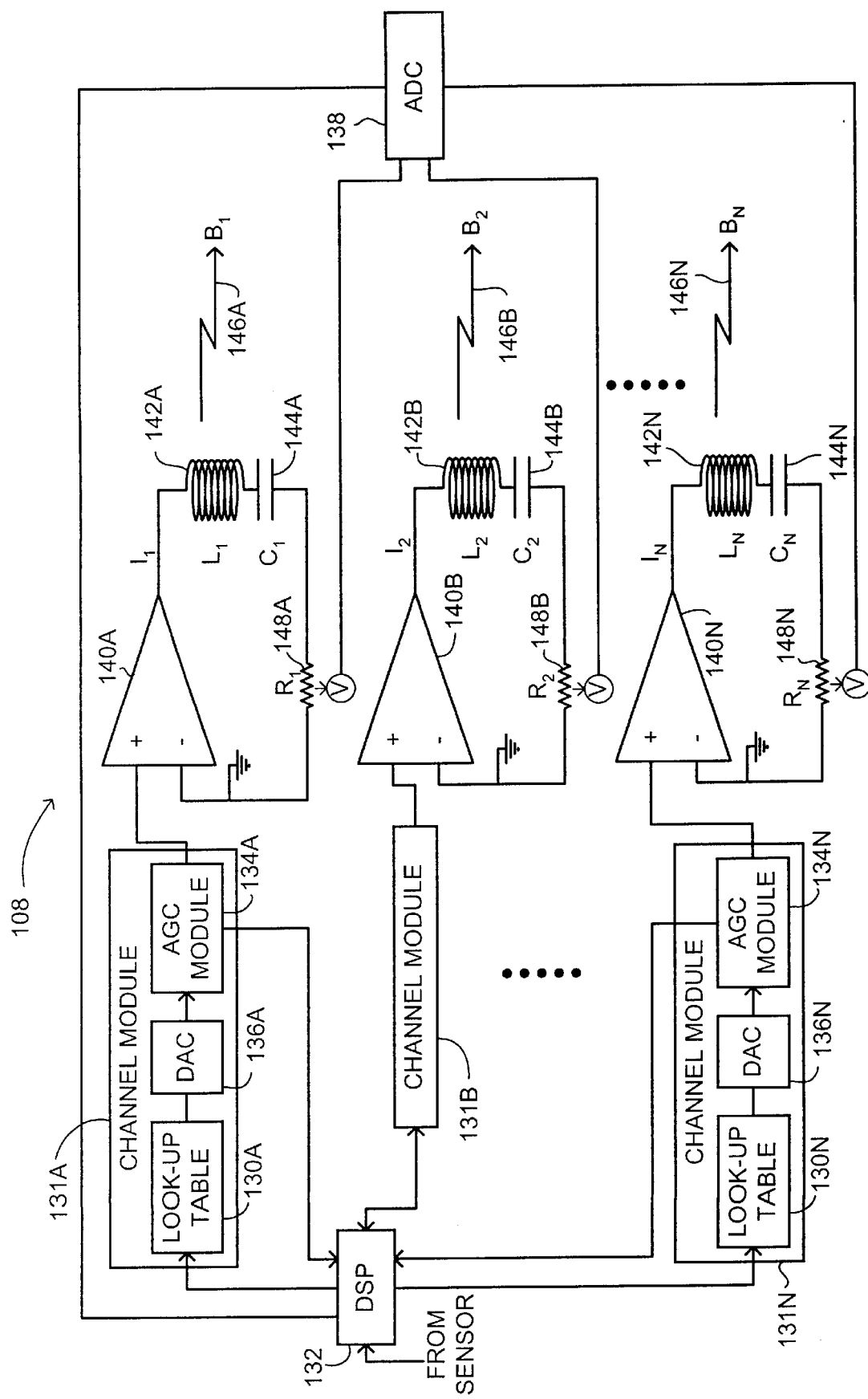
FIG. 6 is a schematic illustration in detail of the electromagnetic generator section of a positioning system, constructed and operative in accordance with another preferred embodiment of the present invention.

Reference is now made to FIG. 6, which is a schematic illustration in detail of the electromagnetic generator 108 section of a system 100, constructed and operative in accordance with further preferred embodiment of the present invention.

Electromagnetic generator 108 includes a digital signal processor (DSP) 132, a plurality of channel modules, generally referenced 131, an analog to digital converter 138, three amplifiers 140A, 140B and 140N, three coils 142A, 142B and 142N, three capacitors 144A, 144B and 144N and a plurality of precise resistors 148A, 148B and 148N. Coils 142A, 142B and 142N have values $L_1$, $L_2$ and $L_3$, respectively. Capacitors 144A, 144B and 144N have capacitance values of $C_1$, $C_2$ and $C_3$, respectively. Resistors 148A, 148B and 148N have resistance values of $R_1$, $R_2$ and $R_3$ respectively. It is noted that the system 108 uses capacitors 144A, 144B and 144N so as to be operated in resonance modes. It is noted that system 108 can be operated in non-resonance modes, for addressing a wide band of transmission frequencies, when the capacitors 144A, 144B and 144N are removed and the coils are directly connected to the resistors.

Each of the cannel modules 131 includes a look-up table module, generally referenced 130, a digital to analog module, generally referenced 136 and an automatic gain control (AGC) module, generally referenced 134. It is noted that each of the channel modules controls a magnetic generation unit, and hence a magnetic field generation channel.

DSP 132 and the DAC 136 are each connected to the look-up table module 130 and to the AGC module 134. The AGC module is further connected to the positive input ports of amplifiers 140A, 140B and 140N. Each of the coils 142A, 142B and 142N is connected between an output of a respective one of the amplifiers 140A 140B and 140N and a respective one of the capacitors 144A, 144B and 144N. Each of the precise resistors 148A, 148B and 148N is connected between the capacitors 144A, 144B and 144N and the negative input of a respective amplifier 140A, 140B and 140N. Coils 142A, 142B and 142N are positioned in different directions, to each other. It is noted that the DSP 132 receives feedback from the coils 142A 142B and 142C, using the precise resistors 148A, 148B and 148N. The ADC converter 138 is connected to a plurality of voltage measurement units 150A, 150B and 150N, each measuring the voltage across a selected one of the resistors 148A, 148B and 148N. The ADC 138 is further connected to the DSP 132.

Each of the power amplifiers 140A, 140B and 140N drives a respective current $I_1$, $I_2$ and $I_3$ through a respective coil 142A, 142B and 142C, thereby generating three respective magnetic fields $B_1$, $B_2$ and $B_3$. Sensor 110 (FIG. 1B) simultaneously detects a magnetic signal which includes these three magnetic fields $B_1$, $B_2$ and $B_3$, which are translated to voltage in each of the coils 152, 154 and 156 of sensor 110. It is noted that the system 100 can include additional magnetic field generators and hence can generate additional magnetic fields. The produced voltage signals are:

$$V_x(t)=X_1\times\sin(\omega_1 t)+X_2\times\sin(\omega_2 t)+\ldots+X_N\times\sin(\omega_N t)$$

$$V_y(t)=Y_1\times\sin(\omega_1 t)+Y_2\times\sin(\omega_2 t)+\ldots+Y_N\times\sin(\omega_N t)$$

$$V_z(t)=Z_1\times\sin(\omega_1 t)+Z_2\times\sin(\omega_2 t)+\ldots+Z_N\times\sin(\omega_N t)$$

The detector voltage amplitude matrix (for a 3×3 example) is:

$$Amp = \begin{bmatrix} X_1 & X_2 & X_N \\ Y_1 & Y_2 & Y_N \\ Z_1 & Z_2 & Z_N \end{bmatrix}$$

the present example, provides an explanation which addresses a three channel case. It is noted that the invention is not limited to the number of channels, and can be easily expanded as desired. Additional channels increase the level of accuracy of the detection of the location of the sensor. A plurality of measurements, produced from a plurality of transmitters, each at a different location, provide a lot of information, which can be used to eliminate distortions, interference and the like.

According to the present invention, this matrix is measured continuously at the detector end. At the same time, the currents $I_1$, $I_2$ and $I_3$, are measured at the transmitting end. Hence, since both the transmission and the reception processes are executed at the same time, then the system 100 can determine the location of the detector with respect to the transmitter at a fast refresh rate, which is in the order of 10 ms or less.

In accordance with a further aspect of the invention, the currents $I_1$, $I_2$ and $I_N$ are measured using precise value resistors, which are connected in with each of the coils 142A, 142B and 142N. Measuring the voltage across these resistors yields a precise determination of the currents therein. The measurements of the voltage values is provided in digital form from the ADC 138 to the DSP 132.

In accordance with another aspect of the invention, a special hardware structure is used to improve the speed and quality of the sinusoidal waveform of the generated magnetic fields. The DSP 132 determines the signal, which is to be transmitted by each of the coils 142A, 142B and 142N. Each of these signals includes a combination of a plurality of simple waveforms, such as sinusoids and the like. The DSP 132 can further determine a sequence in which each of the waveforms is to be transmitted. It is noted that according to the present invention, the signals can be transmitted simultaneously.

The DSP 132 stores the waveforms in the look-up table 130. The look-up table 130 eliminates the need for the DSP 132 to compute waveforms during operation of the system. The waveforms are stored in a continuous wave format, where they can be retrieved directly from the look-up table and transmitted endlessly.

When the system is initiated, then the DSP 132 transmits a sequence of test signals and detects combines the selected numeric representations and produces a numeric representation, which is a summation thereof. At this point, the DSP 132 provides the summed numeric representation to the DAC 136, via the look-up table 130. The DAC 132 produces a respective analog signal for each of the coils 142A, 142B and 142N and provides it to the respective amplifier 140A, 140B and 140N. The DSP 132 detects signals, which are received on the transmitting coils, respective of cross talk and other interference. At this stage, the DSP 132 can recalculate the waveforms, thereby compensating for the detected interference and update the look-up table 130, accordingly.

Figure 7:
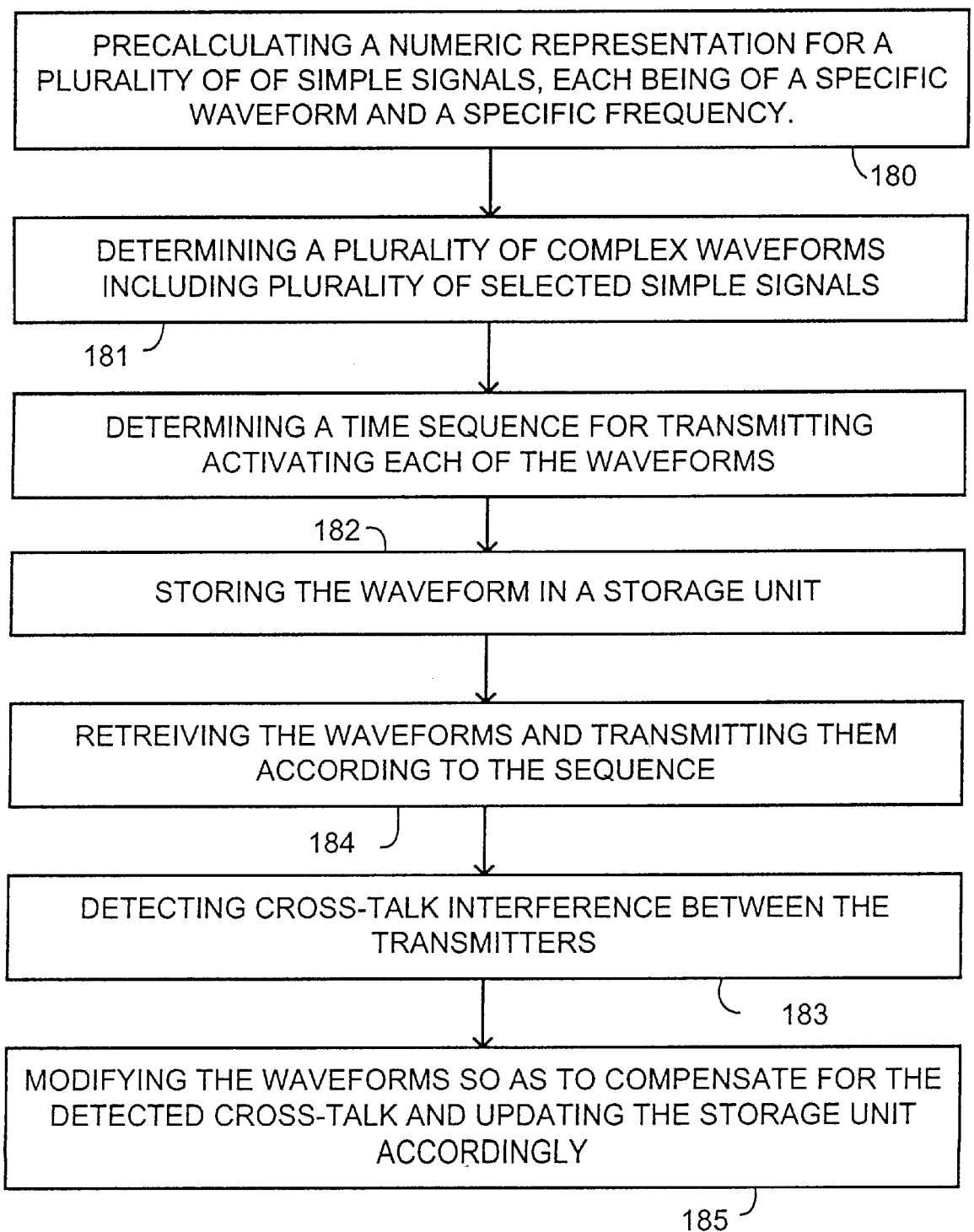
FIG. 7 is a schematic illustration of a method for generating a complicated magnetic field waveform, operative in accordance with a further preferred embodiment of the present invention.

Reference is now made to FIG. 7, which is a schematic illustration of a method for generating a complicated magnetic field waveform, operative in accordance with another preferred embodiment of the present invention. In step 180, a plurality of numeric representations, of simple signals are computed.

In step 181, a plurality of complex waveforms, each including a plurality of selected simple signals is determined. Each of the waveforms, is basically a super-positioning of a plurality of such simple waveforms at selected frequencies. For example, such a complex waveform can include:

$$S_{complex}(t)=A_1\times\sin(1000\pi\cdot t)+A_2\times\sin(1100\pi\cdot t)+A_3\times\sin(1500\pi\cdot t)$$

It is noted that a complex waveform signal can include as many simple signals as desired. In general, this depends on many factors such as the power of the determining DSP, the speed of the communication between the various components of the system, the accuracy specified for the system and the like. At this point the DSP 132 processes the wave forms, with respective parameters, such as amplitude, offset and the like thereby producing a numeric expression of the complex waveform. It is noted that the DSP 132 can further determine a sequence. for transmitting the waveforms (step 182).

In step 183, the numeric representations of the waveforms are stored in the storage unit, which in the example of system 100 is the look-up table 130.

In step 184 the waveforms are retrieved and transmitted according to the determined sequence. The numeric expression of the complex waveform is converted into an analog signal by the digital to analog converter 136 and transmitted using the transmission section.

In step 185 the DSP detects cross talk and general interference, which are received from the AGC unit 134. Accordingly, the DSP 132 modifies the waveforms so as to compensate for the detected cross talk and updates the storage unit accordingly (step 186). The waveforms stored in the look-up table 130 can now be transmitted continuously. It is noted that only a drastic change in the electromagnetic environment requires repeating of this procedure.

Hence. the present invention eliminates the need to co-compute the numeric representation of each of complex waveforms, which include each of the magnetic field signals, thereby dramatically increasing the speed in which such signals are produced.

The magnetic fields $B_1$, $B_2$ and $B_N$, in each of the coils 142A, 142B and 142C are dependant on the currents $I_1$, $I_2$ and $I_N$, flowing there through. In a physically ideal system there would be independence between $I_1$, $I_2$ and $I_N$. However, any multi dimensional magnetic field generator incorporates some cross talk between the field generating elements. The X direction field generating coil induces currents in the Y and Z direction field generating coils, the Y direction field generating coil induces currents in the X and Z direction field generating coils and the Z direction field generating coil induces currents in the X and Y direction field generating coils. The measured currents are:

$$I_x(t) = \frac{V_1 \cdot \sin(\omega_1 t)}{R_1}; I_y(t) = \frac{V_2 \cdot \sin(\omega_2 t)}{R_2} \text{ and } I_z(t) = \frac{V_N \cdot \sin(\omega_N t)}{R_N}$$

The actual currents, as transformed to voltage across resistors $R_1$, $R_2$ and $R_N$ are:

$$I_x(t) = \frac{V_1 \cdot \sin(\omega_1 t) + B_1 \cdot V_2 \cdot \sin(\omega_2 t) + \ldots + N_1 \cdot V_N \cdot \sin(\omega_N t)}{R_1},$$

$$I_y(t) = \frac{A_2 V_1 \cdot \sin(\omega_1 t) + V_2 \cdot \sin(\omega_2 t) + \ldots + N_2 \cdot V_N \cdot \sin(\omega_N t)}{R_2},$$

and $$I_z(t) = \frac{A_3 V_1 \cdot \sin(\omega_1 t) + B_3 V_2 \cdot \sin(\omega_2 t) + \ldots + V_N \cdot \sin(\omega_N t)}{R_N},$$

where $A_2$, $A_3$, $B_1$, $B_3$, $N_1$ and $N_2$ are predetermined coefficients.

Figure 8:
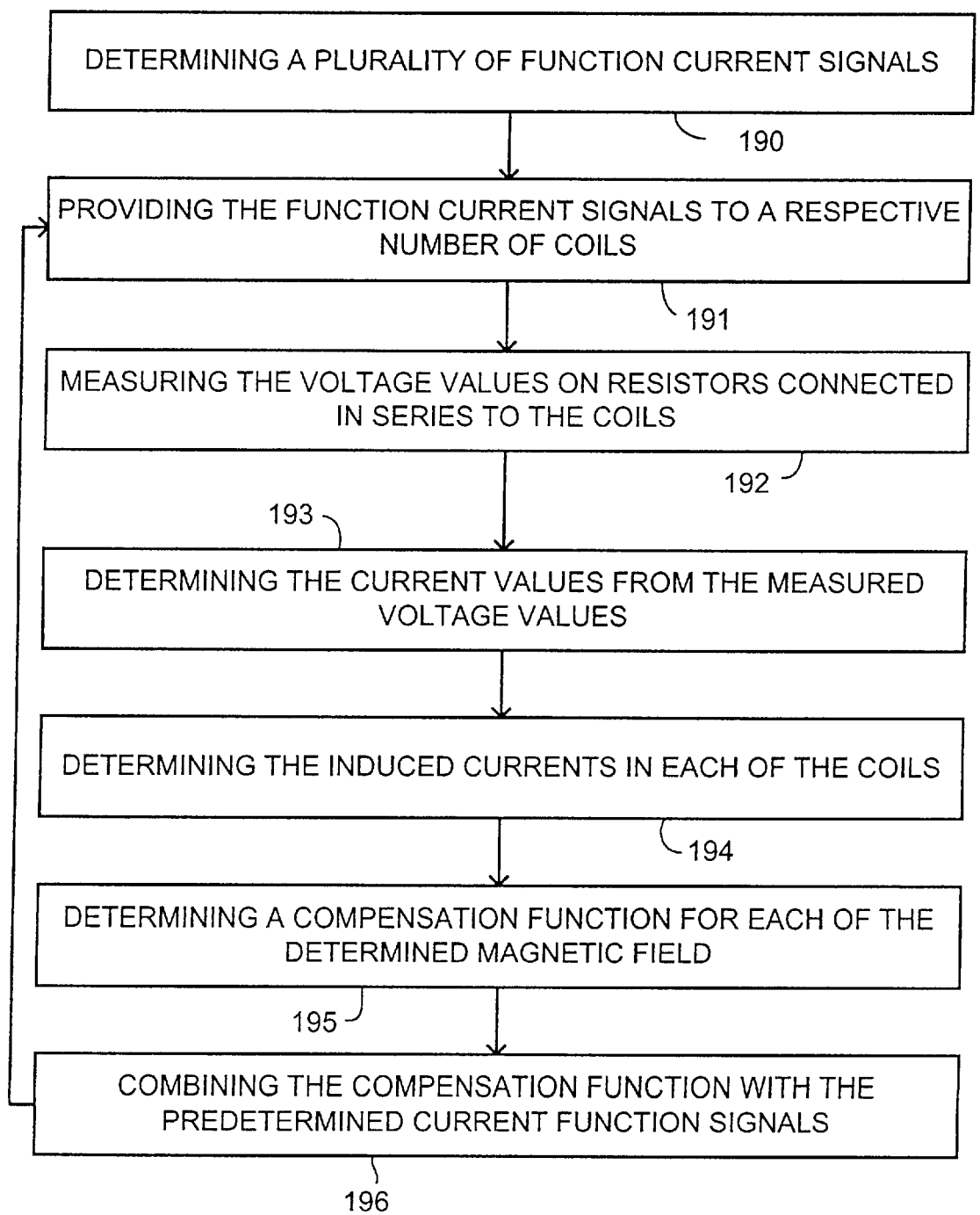
FIG. 8 is a schematic illustration of a method for operating a system, operative in accordance with another preferred embodiment of the present invention.

According to the present invention, system 100 measures the cross-talk components in each axis and provides a respective compensation. In accordance with a further aspect of the invention, there is provided a method for compensating for cross talk between cnannels. Reference is now made to FIG. 8, which is a schematic illustration of a method for operating system 100, operative in accordance with a further preferred embodiment of the invention. At first, the DSP 132 (FIG. 6) determines a plurality of function current signals (step 190), one for each axis. These functions are provided as electrical currents to the coils, which in turn produce magnetic fields (step 191).

In step 192, the system measures the voltage values across the resistors connected in series with each of the coils. It is noted that these are high precision resistors and thus the system 100 can determine an accurate current value, from each of them for a respective one of the axis (step 193).

In step 194, the system 100 determines the induced currents in each of the coils, by subtracting the original function current from the determined current value. In step 195 the DSP 132 determines a compensation function for each of the determined magnetic fields, according to the determined induced currents and combines each of the compensation functions with the respective current function signals (step 196). Finally, the system 100 repeats from step 190

In accordance with another aspect of the present invention, multi-frequency signals are used so as to overcome metal distortions. Each of the coils receives a signal, which includes a different set of frequencies. The signal, which is provided to each of the coils, is of the form:

$$F_i(t) = \sum_{i=1}^{N} A_i \cdot \sin(w_i t)$$

where A is the amplitude vector for each of the frequencies.

Figure 2A:
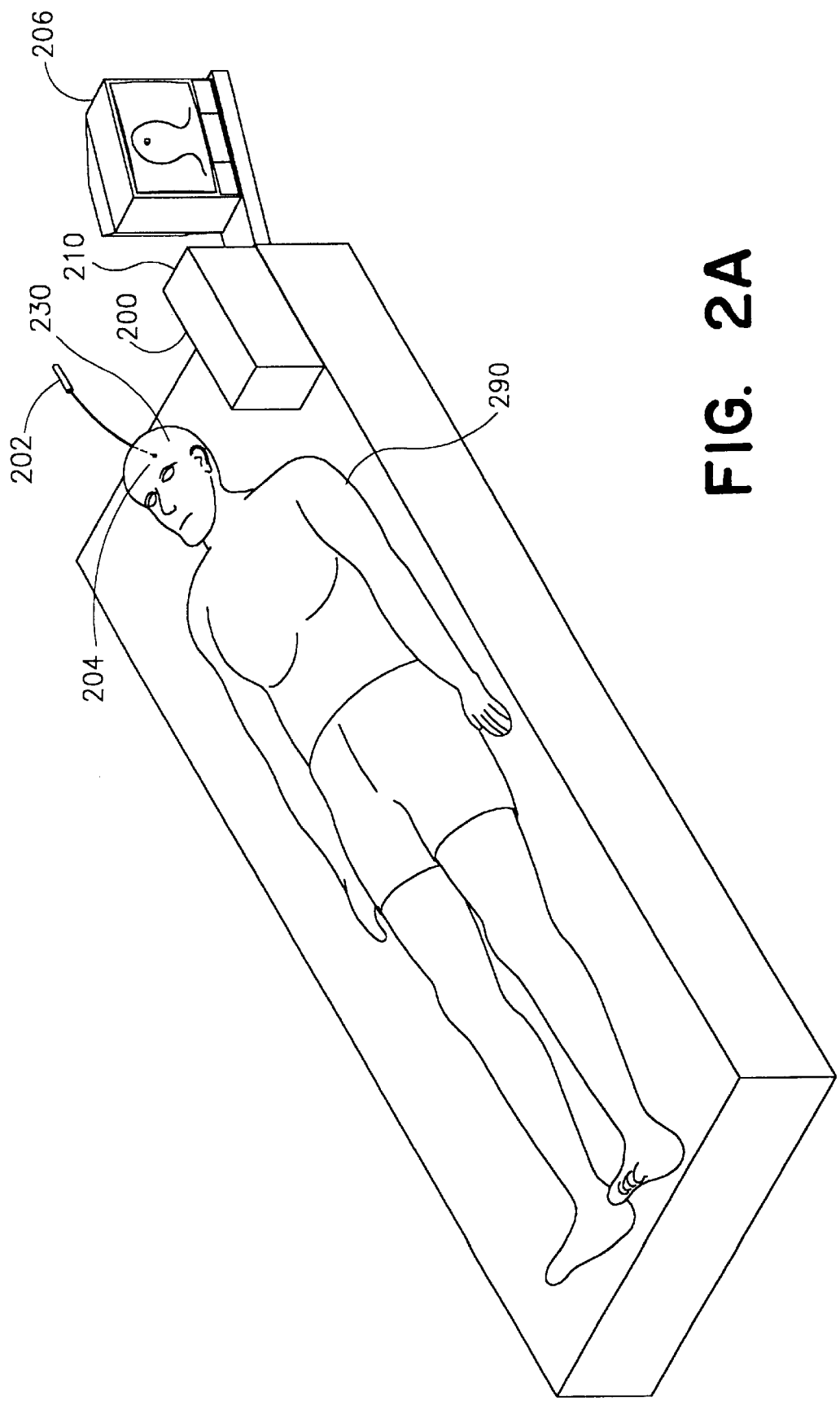
FIG. 2A is an illustration of a patient and an invasive system, constructed and operative in accordance with another preferred embodiment of the invention.
Figure 2B:
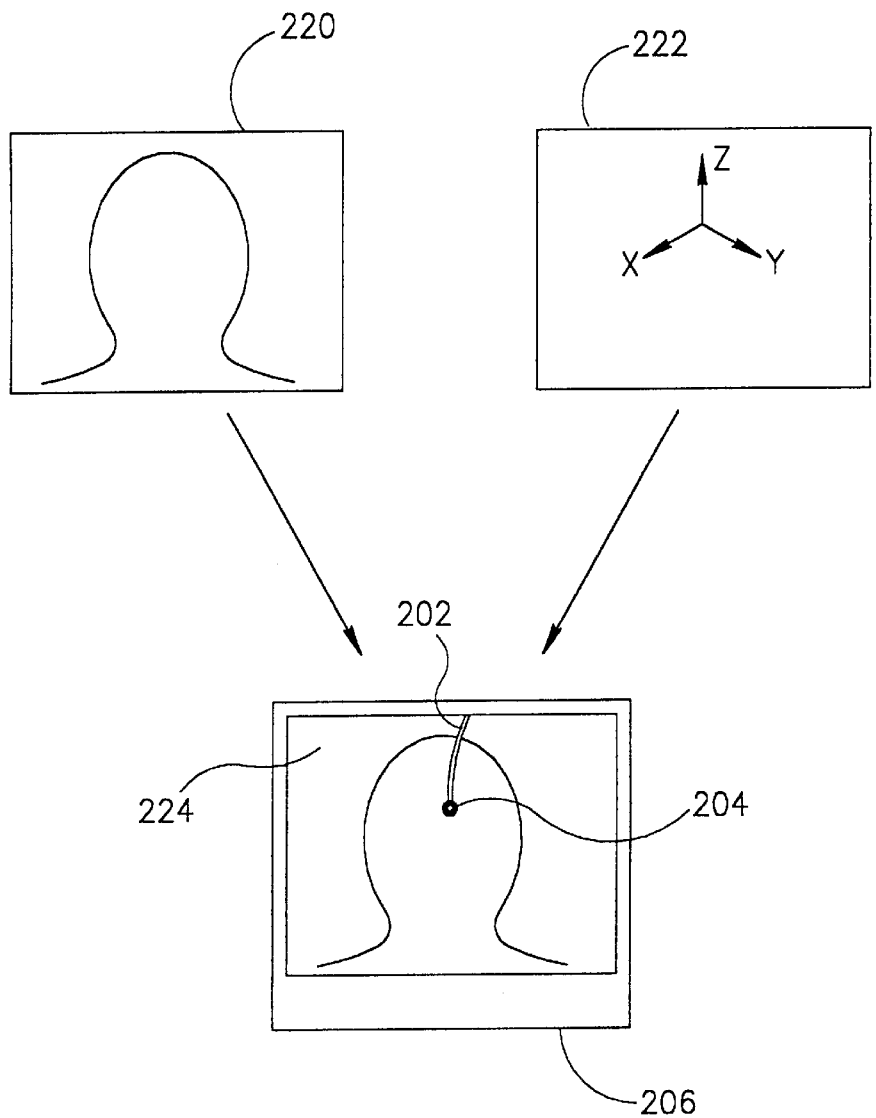
FIG. 2B is an illustration of a 3D image, a positioning representation and the super imposing of both of them.

The system of the present invention can be implemented in any invasive device, which is inserted within a living tissue. Reference is now made to FIGS. 2A and 2B. FIG. 2A is an illustration of a patient and an invasive system, generally referenced 200, constructed and operative in accordance with another preferred embodiment of the invention. FIG. 2B is an illustration of a 3D image, a positioning representation and the super imposing of both of them.

System 200 includes a main unit 210, an invasive device 202 and a display unit 206. Invasive device 202 includes a 3D magnetic sensor 204, which is located on its tip. It is noted that system 200 is generally similar to system 100. The invasive device 202 can be selected from a plurality of invasive devices such as an endoscope, catheters, needles, surgery devices, and the like.

With further reference to FIG. 2B, the sensor 204 detects electromagnetic fields, which are generated within the main unit 210, and produces a respective signal. The system 200 (FIG. 2A) analyses this information and produces a determination of the location and orientation of the sensor 204 (reference 222). It is noted that since the sensor 204 is firmly attached to the tip of invasive device 202, then the determination of location and orientation also indicates the location and orientation of the tip of the invasive device 202.

In the present example, the inspected living tissue is the head (reference 230) of a patient (reference 290). The system 200 combines a pre-scanned image (reference 220) of the inspected living tissue and the location and orientation of the sensor 204 (reference 222), thereby producing a superimposed image 224. Superimposed image 224 provides visual information of the location and orientation of the tip 204 of invasive device 202, within the inspected living tissue 204.

Figure 3C:
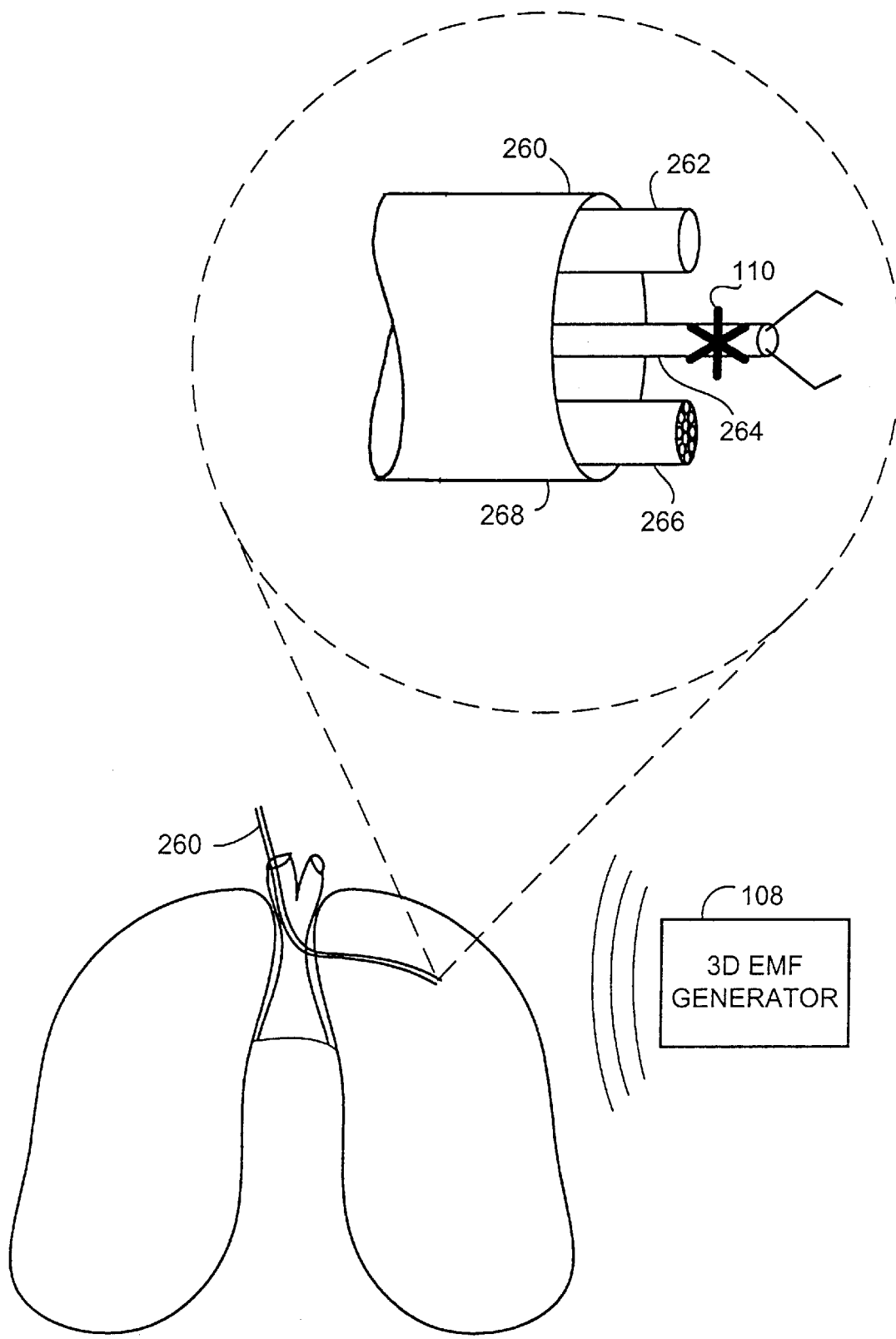

According to this aspect of the invention the system 100 can be mounted on to a bronchoscope. Reference is now made to FIGS. 3A, 3B and 3C, which are illustrations of system 100 of FIG. 1A, incorporated within a bronchoscope, constructed and operative in accordance with a further preferred embodiment of the invention.

FIG. 3A shows a bronchoscope, referenced 260, inserted into the lungs 280 of a patient. A typical bronchoscope includes three main devices, which are a lighting unit, a set of optic fibers for capturing the image at the tip of the bronchoscope and a surgical too. According to the present invention, a bronchoscope further, includes a sensor such as sensor 110, attached to its tip. Reference is further made to FIG. 3C, which is an illustration in detail of the tip of the bronchoscope 260, of FIG. 3A.

Bronchoscope 260 includes an optic fiber 262, a set of optic fibers 266, a surgical tool 264 and sensor 110 of system 100. Optic fiber 262 transfers light from an external source to the tip of the bronchoscope. The set of optic fibers 266 captures the image in the vicinity of the tip and optically conveys this image to an external optical assembly (not shown) for viewing by the physician. The surgical tool 264, which in the present example is a remote controlled clamp, enables the operating physician to perform surgical actions. The sensor 110, being firmly attached to the tip of surgical tool detects the electromagnetic fields in close vicinity of this tip and transfers this information to system 100.

The system 100 analyzes this information and determines the location and orientation (reference 250) of the tip of the surgical tool 264. The system 100 then superimposes the coordinates 250 of the tip of surgical tool 264 264 with a pre-detected image 252 of the treated area, which in the present example, is the lungs 280 of the patient. The outcome 254 is displayed on display unit 114 (FIG. 3B).

It is noted that the diameter of the tip of the dilating catheter 260 is conventionally significantly larger than the diameter of the surgical tool 264. Hence, when the surgical procedure requires accessing areas which are too narrow for the dilating catheter, then the physician can proceed with just the surgical tool, where the location and orientation of the tip of this tool are provided by system 100 264.

According to another aspect of the present invention, the location and orientation detection system, can be combined with a catheter, thereby determining the position of its tip.

Figure 4C:
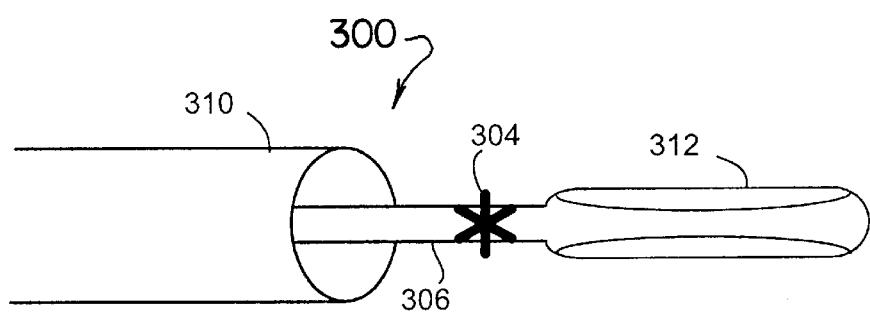
FIG. 4C is an illustration in detail of the tip end of the catheter of FIG. 4A.

Reference is now made to FIGS. 4A, 4B and 4C. FIG. 4A is an illustration of a patient, a catheter and a location and orientation detection system, constructed and operative in accordance with another preferred embodiment of the invention. FIG. 4B is an illustration of the superimposing of the location information 322 provided by the location and orientation detection system of FIG. 4A and a three dimensional image 320 of a treated portion of the body of the patient. FIG. 4C is an illustration in detail of the tip end of the catheter of FIG. 4A.

Catheter 310 is a general dilation catheter, which is used to guide a specific device to the vicinity of the area to be treated. The physician operating the system inserts a mounting catheter 306, which includes a balloon mechanism 312. A sensor 304 is firmly attached to the end of the mounting catheter 306.

The sensor 304 detects electromagnetic fields (produced by generator 302) in a plurality of directions and provides information to the processing unit 308 of system 300. The processing unit 308 analyzes this information, thereby determining the location and orientation of the sensor 304. The system 300 uses these coordinates to produces a superimposed image of the treated area (reference 324).

Figure 5:
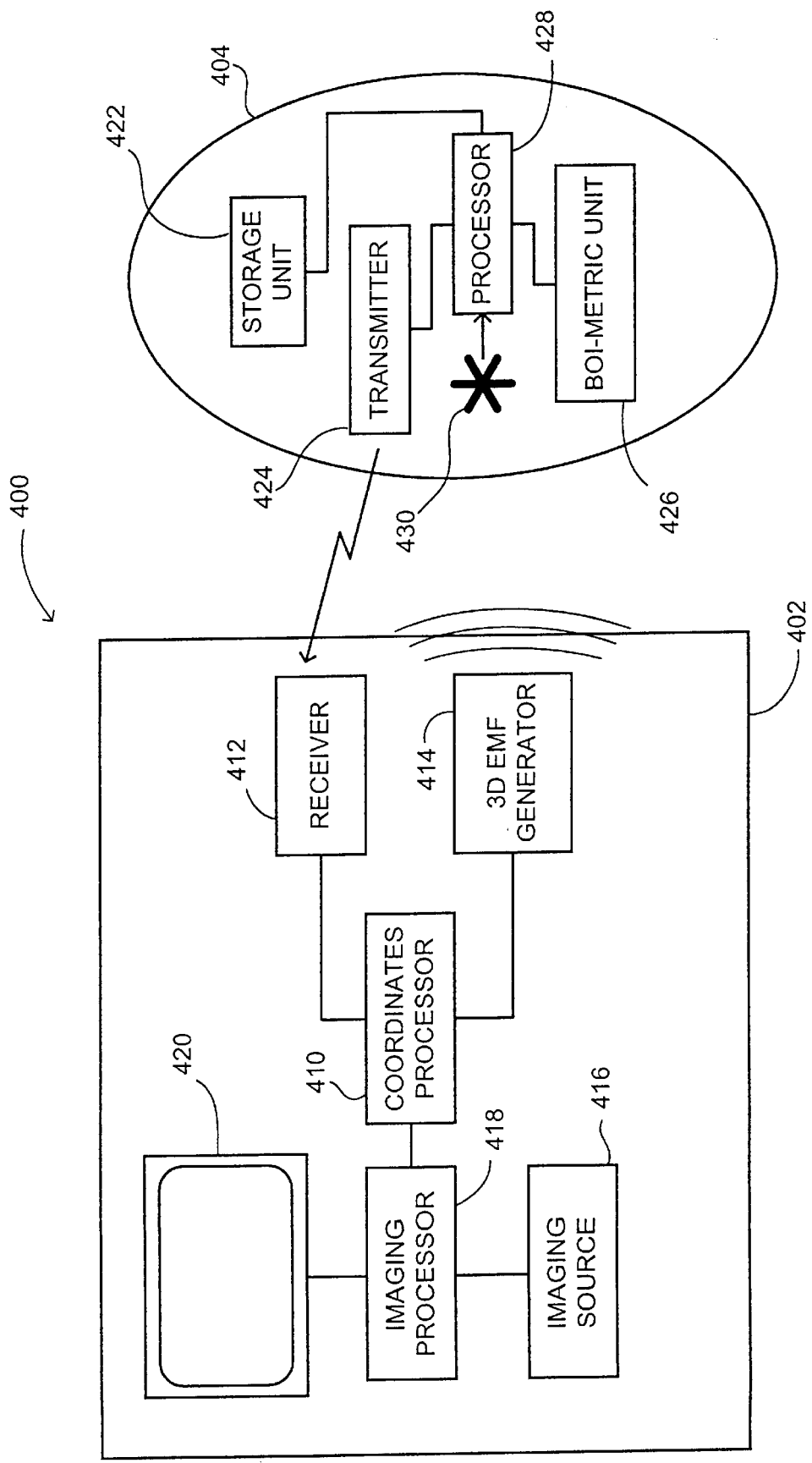
FIG. 5 is a schematic illustration of an inspection system, constructed and operative in accordance with a further preferred embodiment of the present invention

According to the present invention, the communication between the electromagnetic sensor and the analysis unit of the system can be in a wired or wireless manner. Reference is now made to FIG. 5, which is a schematic illustration of an inspection system, generally referenced 400, constructed and operative in accordance with another preferred embodiment of the invention.

System 400 includes a base unit 402 and a remote unit 404. The base unit 402 includes a receiver 412, a three dimensional electromagnetic field generator 414, a coordinate processor 410, an imaging processor 418, and imaging source 416 and a display unit 420. The coordinate processor 410 is connected to the receiver 412, the three-dimensionaL electromagnetic field generator 414 and the imaging processor 418. The imaging processor 418 is further connected to the display unit 420 and to the imaging source 416.

The remote unit 404 includes a storage unit 422, a transmitter 424, a processor 428, a three-dimensional electromagnetic field sensor 430 and a biometric unit 426. The processor 428 is connected to the storage unit 422, the transmitter 424, the three-dimensional electromagnetic field sensor 430 and the biometric unit 426. It is noted that the base unit 402 can use any information received therein. with respect to the detected magnetic fields, so as to modify the electromagnetic fields, which are transmitted by generator 414.

The biometric unit 426 is designed to perform an inner operation on the living tissue. It is noted that such a biometric unit can include an image detector such as a camera, a substance releasing unit for releasing materials at predetermined locations, according to the location and orientation of unit 404, a sampling unit such an oxymeter. The biometric unit can further include a glucometer, a thermometer, an acidity detector and any other physiological probe which can detect predetermined properties of pre-specified tissues of the examined living tissue. According to another aspect of the present invention, biometric units of several types are included in unit 404, such as a physiological probe and a video camera which detects the image of a specified organ of the examined patient.

The physiological probe provides information, with respect to the detected characteristics, to the processor 428. It is noted that the processor can perform an interim analysis of this information, so as to determine if this physiological data is to be transmitted to the base unit 402.

At the same time, the sensor 430 detects electromagnetic field properties in a plurality of directions and provides the detection results to the processor 428. The electromagnetic fields are produced by the three-dimensional electromagnetic field generator 414. It is noted that the system 400 can include a plurality of three-dimensional electromagnetic field generators, such as the one referenced 414. The use of additional electromagnetic field generators enhances the location and orientation measurements accuracy.

The processor 428 packs the detection results with the physiological data and transmits it to the receiver 412, using the transmitter 424. It is noted that the processor 428 can also store selected portions of the data received from the physiological probe 426 and the sensor 430, in the storage unit 422.

The receiver 412 provides the received data to the coordinate processor 410. The processor 410 extracts the data, which relates to the detected electromagnetic fields and determines the location and orientation of the sensor 430 at the time of detection The processor 410 provides the coordinate location data to the imaging processor 418, together with the physiological data. The imagine processor 418 uses this data together with a three dimensional image received from the imaging source 416, to produce a superimposed image and displays it on the unit 420.

Such a superimposed image can include the trail of acidity within the digestion system of the examined patient, where at each point of the journey of the remote unit, both location and acidity level are detected and recorded.

The remote unit 404 is basically designed to be inserted into the body and move about, with minor intervention from the physician. For example, the remote unit 404 can be designed as a capsuie which can be taken through the mouth, make its way through the digestion system of the patient, sampling various properties along the way, and transmit the findings along with the accurate location from which they were taken.

Figure 9:
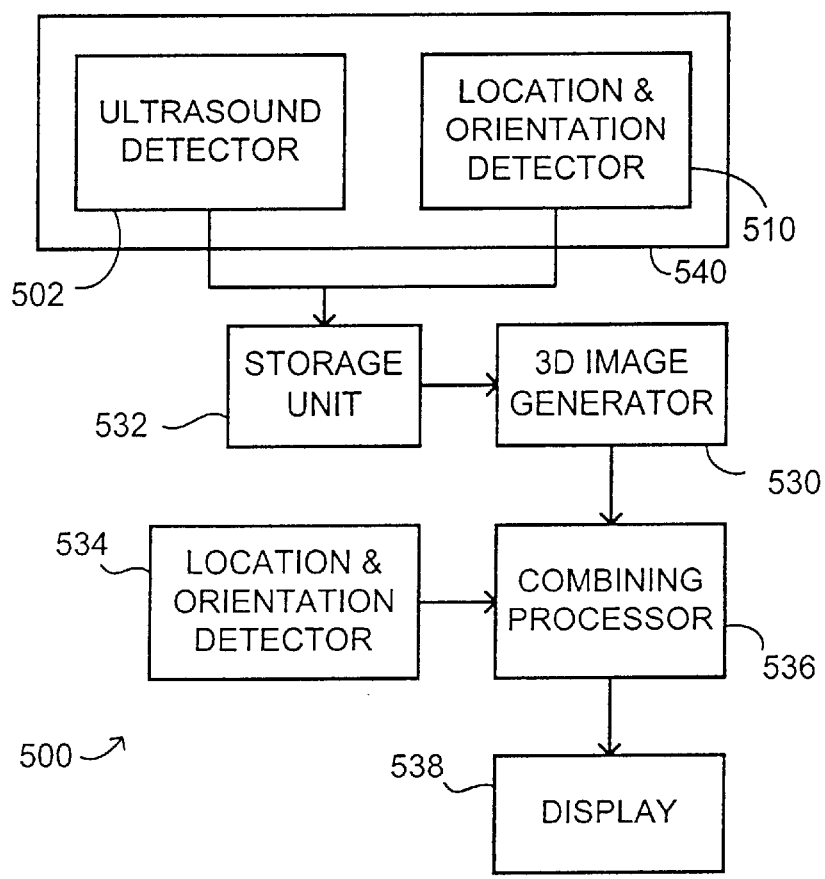
FIG. 9 is a schematic illustration of a three dimensional imaging system, which combines an inner ultrasound transceiver and a location and orientation detector, constructed and operative in accordance with a further preferred embodiment of the present invention.

In accordance with a further aspect of the invention, the position and orientation device is combined with an inner body ultrasound transceiver, thereby providing a real-time three dimensional image generation system. Reference is now made to FIG. 9, which is a schematic illustration of a three dimensional imaging system, which combines an inner ultrasound transceiver and a location and orientation detector, generally referenced 500, constructed and operative in accordance with another preferred embodiment of the invention.

System 500 includes an inner body ultrasound assembly 540, a storage unit 532, a three-dimensional image generator 530, a combining processor 536, a general location and orientation detector 534 and a display unit 536. The inner body ultrasound assembly 540 includes an ultrasound detector 502 and a location and orientation detector 510, which are firmly attached to each other. It is noted that detector 502 can be replaced with any type of ultrasound transceiver of sensor, such as an inner vascular ultrasound (IVUS) element, and the like. The inner body ultrasound assembly 540 is connected to the storage unit 532. The three-dimensional image generator 530 is connected to the storage unit 532 and to the combining processor 536. The combining processor 536 is further connected to the general location and orientation detector 534 and to the display unit 538. It is noted that the storage unit 532 is redundant when the three-dimensional image generator 530 is powerful enough for real-time image processing. In this case, the inner body ultrasound assembly 540 is directly connected to the three-dimensional image generator 530.

The inner body ultrasound assembly 540 detects a plurality of two dimensional ultrasound images, and a plurality of location and orientation readings of the ultrasound detector 502, each associated with a selected one of the two dimensional ultrasound images. Each of the two dimensional ultrasound images presents a different slice of a scanned three-dimensional volume. Each such pair of a two-dimensional ultrasound image and a location and orientation reading of the ultrasound detector is stored, as a record, in storage unit 532. It is noted that the location and orientation detector 510 can operate according to the electromagnetic methods, which are presented according to the present invention, as well as according to any other electromagnetic method which is known in the art, such as rotating field, simple magnetic feedback and the like.

The three-dimensional image generator 530 retrieves the records and produces a three dimensional representation of the scanned volume. This representation can be further combined with location and orientation data provided from another location and orientation detector which is associated with any surgical tool such as a camera, clamps, a laser device and the like. The final result, including a three dimensional representation of the scanned volume, combined with an indication of the location and orientation of the surgical tool. is displayed on display unit 538.

Figure 10C:
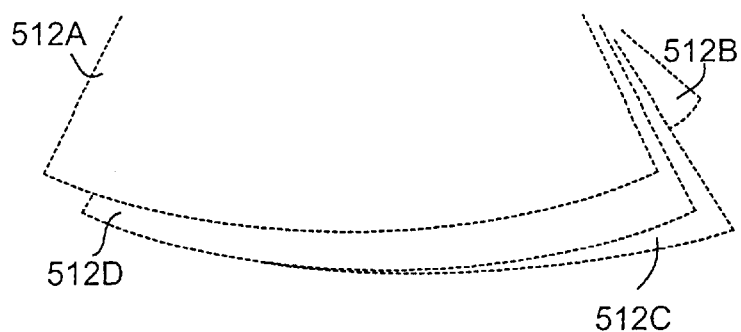
FIG. 10C is an illustration in perspective of a plurality of angular ultrasound slice images.
Figure 10A:
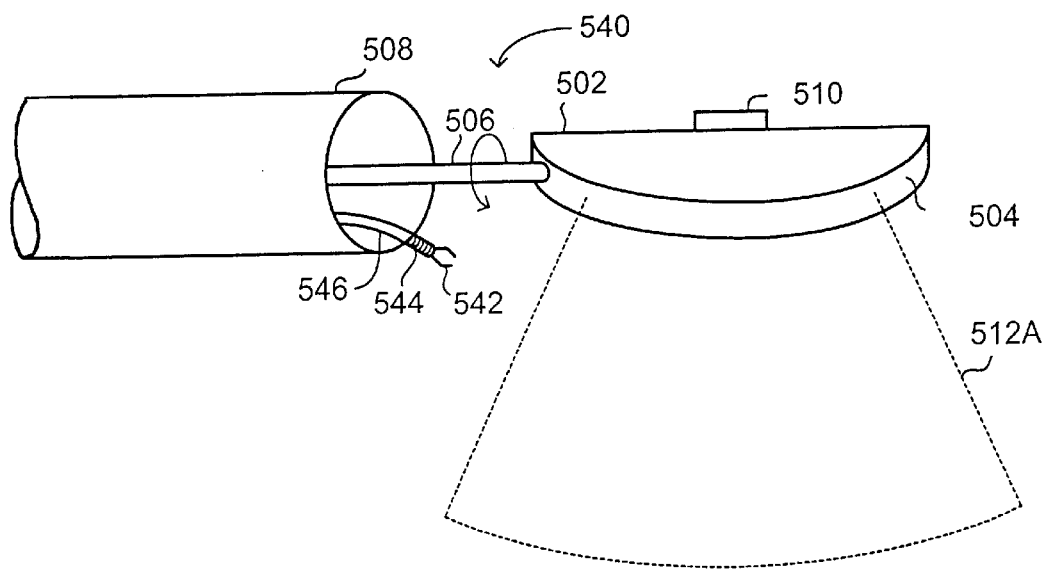
FIGS. 10A and 10B are illustrations in perspective of an inner body ultrasound assembly of FIG. 9, constructed and operative in accordance with another preferred embodiment of the present invention.
Figure 10B:
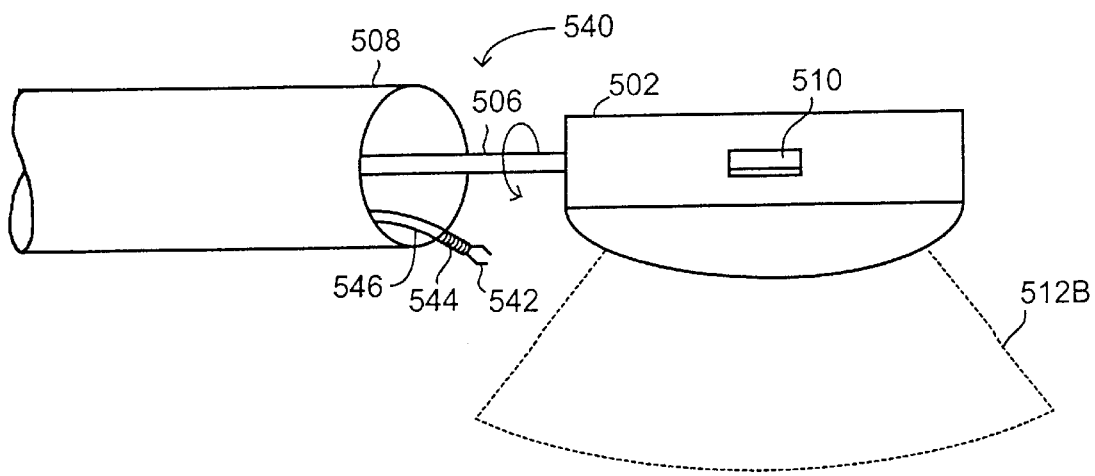

Reference is now made to FIGS. 10A and 10B, which are illustrations in perspective of an inner body ultrasound assembly 540, of FIG. 9, constructed and operative in accordance with another preferred embodiment of the invention. System 540 further includes a dilation catheter 508, a mounting catheter 506 and a surgical tool 542. The ultrasound transceiver 502 is fixed to the mounting catheter 506, which is inserted in the dilation catheter 508. The location and orientation detector 510 is attached to the rear side of the ultrasound transceiver 502. The surgical tool 542 includes clamps, where the location and orientation detector 544 surrounds the tip of the guiding tube 546 thereof The location and orientation detector 510 continuously detects the location and orientation of the ultrasound transceiver 502. The ultrasound transceiver 502 continuously transmits and detects ultrasound waves, from its front end 504, thereby generating an angular ultrasound slice image, generally referenced 512A. The image 512A is a two dimensional representation of the objects which are located in front of section 504.

With reference to FIG. 10B, the user can direct the ultrasound transceiver 502 in various directions, for example by means of rotation, thereby producing additional angular ultrasound slice images such as the one denoted 512B. Reference is now made to FIG. 10C, which is an illustration in perspective of a plurality of angular ultrasound slice images, generally referenced 512. The angular ultrasound slice images 512A (FIG. 10A), 512B (FIG. 10B), 512C and 512D are two-dimensional representations of various sections of the scanned volume. These images are combined to a three dimensional image, by the three-dimensional image generator 530.

It is noted that using system 500, the physician can operate on the patient immediately after creating the image of the treated area and further update the image, at any desired moment, thereafter.

Figure 11A:
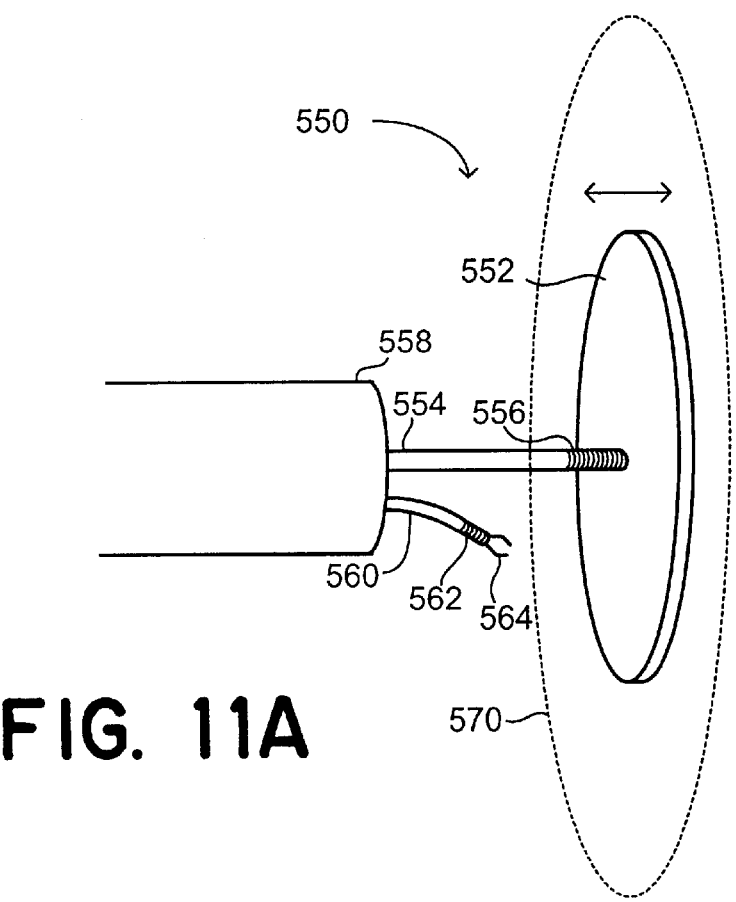
FIGS. 11A and 11B are illustration in perspective of an inner body ultrasound assembly, constructed and operative in accordance with a further preferred embodiment of the invention.
Figure 11B:
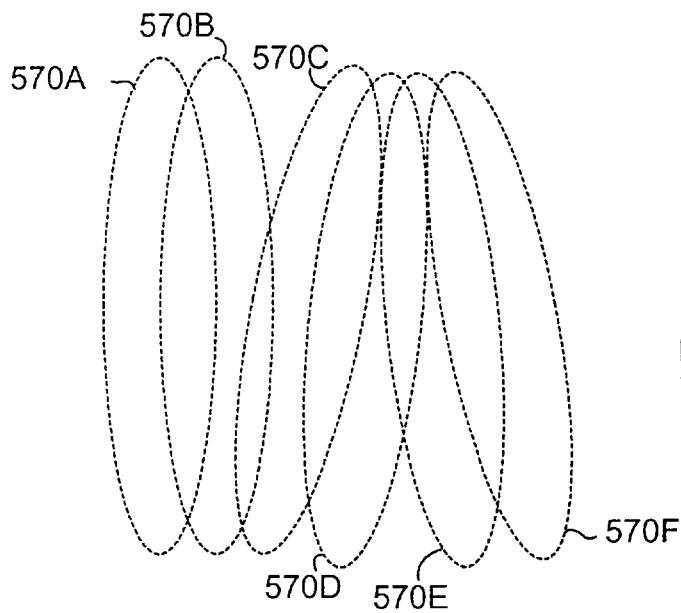

Reference is now made to FIGS. 11A and 11B, which are illustration in perspective of an inner body ultrasound assembly, generally referenced 550, constructed and operative in accordance with another preferred embodiment of the invention. Inner body ultrasound assembly 550 includes a radial ultrasound transceiver 552 and a location and orientation detector 556. The radial ultrasound transceiver 552 is mounted on a mounting catheter 554, which is further inserted in a dilation catheter 558. The location and orientation detector 556 is located at the tip of the mounting catheter 554, near the base of the radial ultrasound transceiver 552. As can be seen in FIG. 11A, the location and orientation detector 556 includes a single coil, which is twisted around the tip of the mounting catheter 554. The inner body ultrasound assembly 550 can replace the inner body ultrasound assembly 540 of FIG. 9. The operating user can move the inner body ultrasound assembly 550 back and forth (denoted by a bi-directional arrow) as well as in various directions as will be further illustrated in FIG. 11B, herein below.

The location and orientation detector 556 continuously detects the location and orientation of the tip of the mounting catheter 554, and hence, the location and orientation of the base of the radial ultrasound transceiver 552. The location and orientation detector 556 provides the detected information to the storage unit 532 (FIG. 9). The radial ultrasound transceiver 552 continuously detects a radial ultrasound slice image, generally referenced 570. The radial ultrasound transceiver 552 provides the detected image information to the storage unit 532.

The storage unit 532 includes a plurality of records, each including a two dimensional radial slice of the scanned volume and a location and orientation or a predetermined point with respect to that slice. Reference is now made to FIG. 11B, which is an illustration in perspective of a plurality of radial ultrasound slice images, generally referenced 570. Radial angular ultrasound slice images 570A, 570B, 570C, 570D, 570E and 570F are two-dimensional representations of various sections of the scanned volume. These images are combined to a three dimensional image, by the three-dimensional image generator 530.

Figure 12:
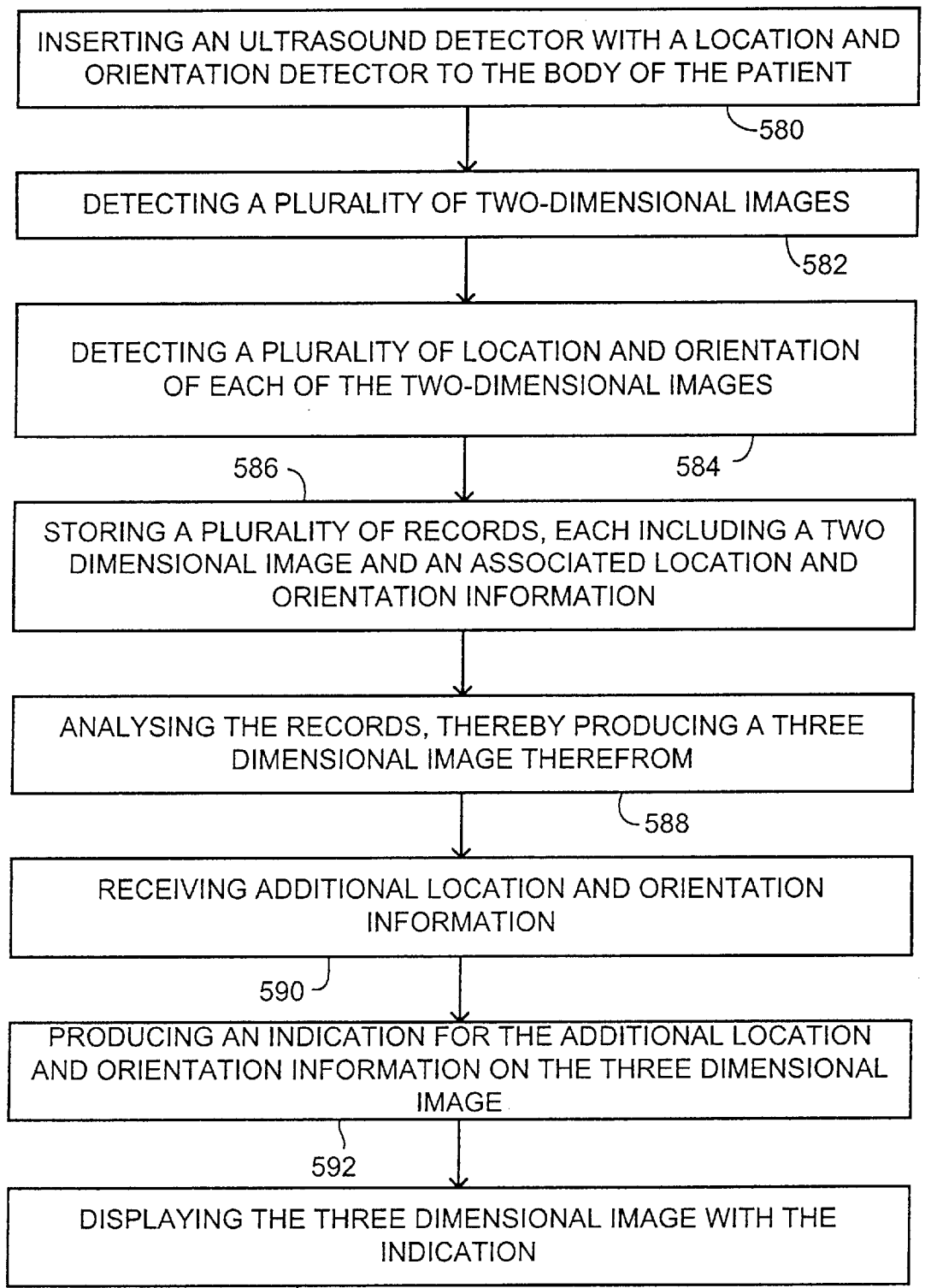
FIG. 12 is a schematic illustration of a method for operating a system, operative in accordance with another preferred embodiment of the invention.

Reference is now made to FIG. 12, which is a schematic illustration of a method for operating system 500, operative in accordance with a further preferred embodiment of the invention. In step 580, the ultrasound detector 502 with the location and orientation detector 510 are inserted into the body of the patient and located at the area to be inspected and treated. In step 582 the ultrasound detector 502 detects a plurality of two-dimensional images (references 512 in FIG. 9C). In step 584, the location and orientation detector 510 detects the location and orientation of each of the two-dimensional images.

In step 586, records, which include image and location and orientation information, are stored. It is noted that this step is redundant, provided the three-dimensional image generator is powerful enough. In step 588, the three image generator 530 processes the records thereby producing a three dimensional representation of the scanned volume. This image, produced from the inner part of the scanned volume can now be displayed. For example, an inner body ultrasound assembly using MPS sensor with an IVUS can be used to produce reconstructed three-dimensional images of blood vessels.

In step 590, the system receives additional location and orientation information which are originated from a different location and orientation detector, associated with any of a plurality of surgical tools. Such a surgical tool can be selected from the list consisting of any type of operational catheter, a camera, a lighting device and the like. It is noted that the present invention is not limited to one additional location and orientation sensor, rather a plurality of such sensors can be incorporated in a single system, where each is indicated on the three dimensional image (step 592) and displayed thereafter (step 594).

In accordance with a further aspect of the invention, there is provided a method for positioning a location and orientation detector on a reference image, prior to maneuvering it inside the body of the patient.

Figure 13:
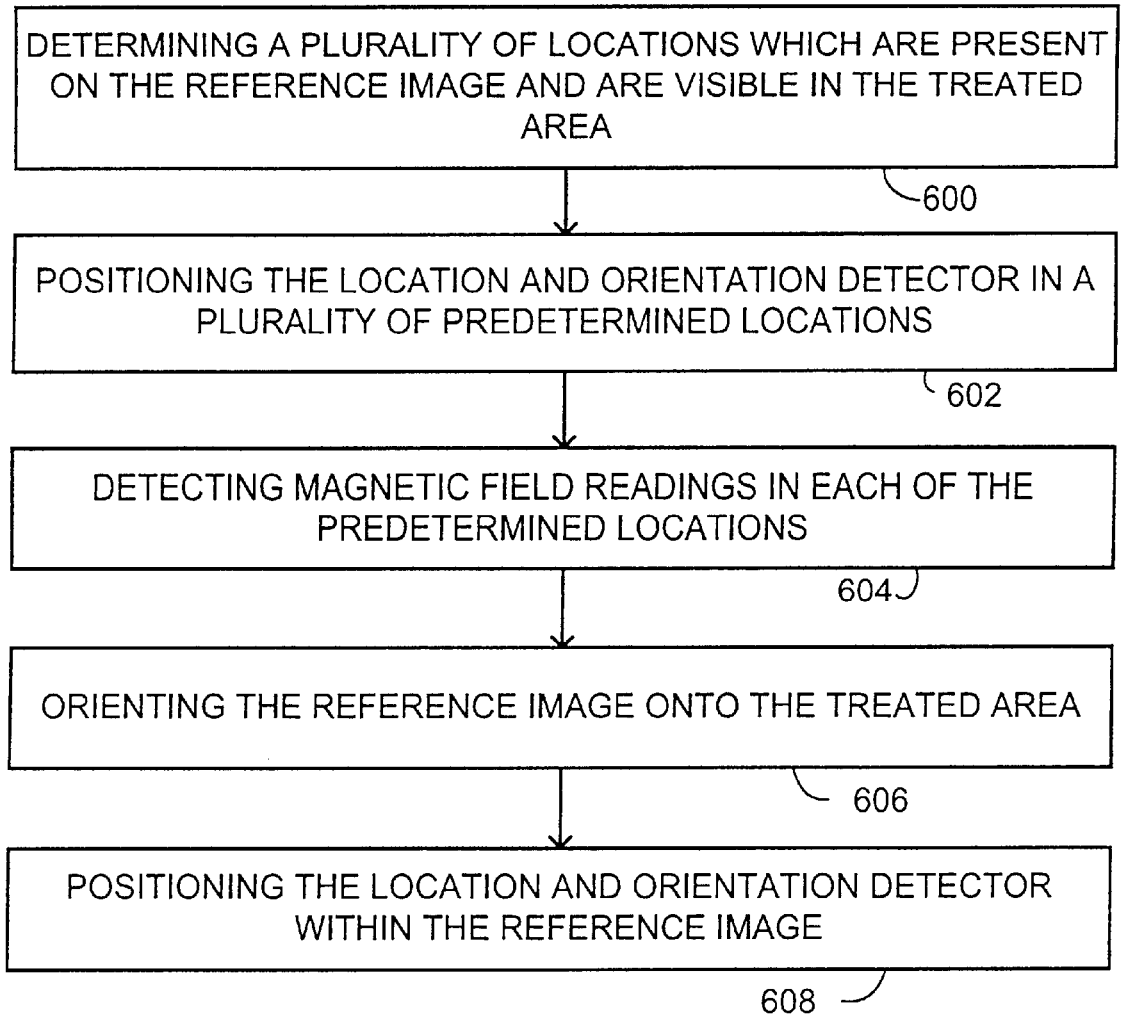
FIG. 13 is a schematic illustration of a method for initially positioning a location and orientation detector onto a reference image, operative in accordance with a further preferred embodiment of the present invention.

Reference is now made to FIG. 13, which is a schematic illustration of a method for initially positioning a location and orientation detector onto a reference image, operative in accordance with a further preferred embodiment of the invention. The method of the present invention utilizes known locations on the treated area, which are visible thereon and also visible on the reference image, which is to be associated therewith. At first, a plurality of such locations is determined (step 600). With respect to FIG. 3B, the main junctions of the lung system are easily detected, so are specific bone areas such as the solar plexus, vocal cords. and the like In step 602, the location and orientation detector is places in each of these locations and a reading is taken accordingly (step 604). It is noted that two or three such locations are enough to position the detector within the reference image. Any more such locations can be used to improve the accuracy of the positioning process. Finally the reference image is oriented onto the treated area (step 606) and the location and orientation detector can be positioned within the reference image (step 608).

Figure 14:
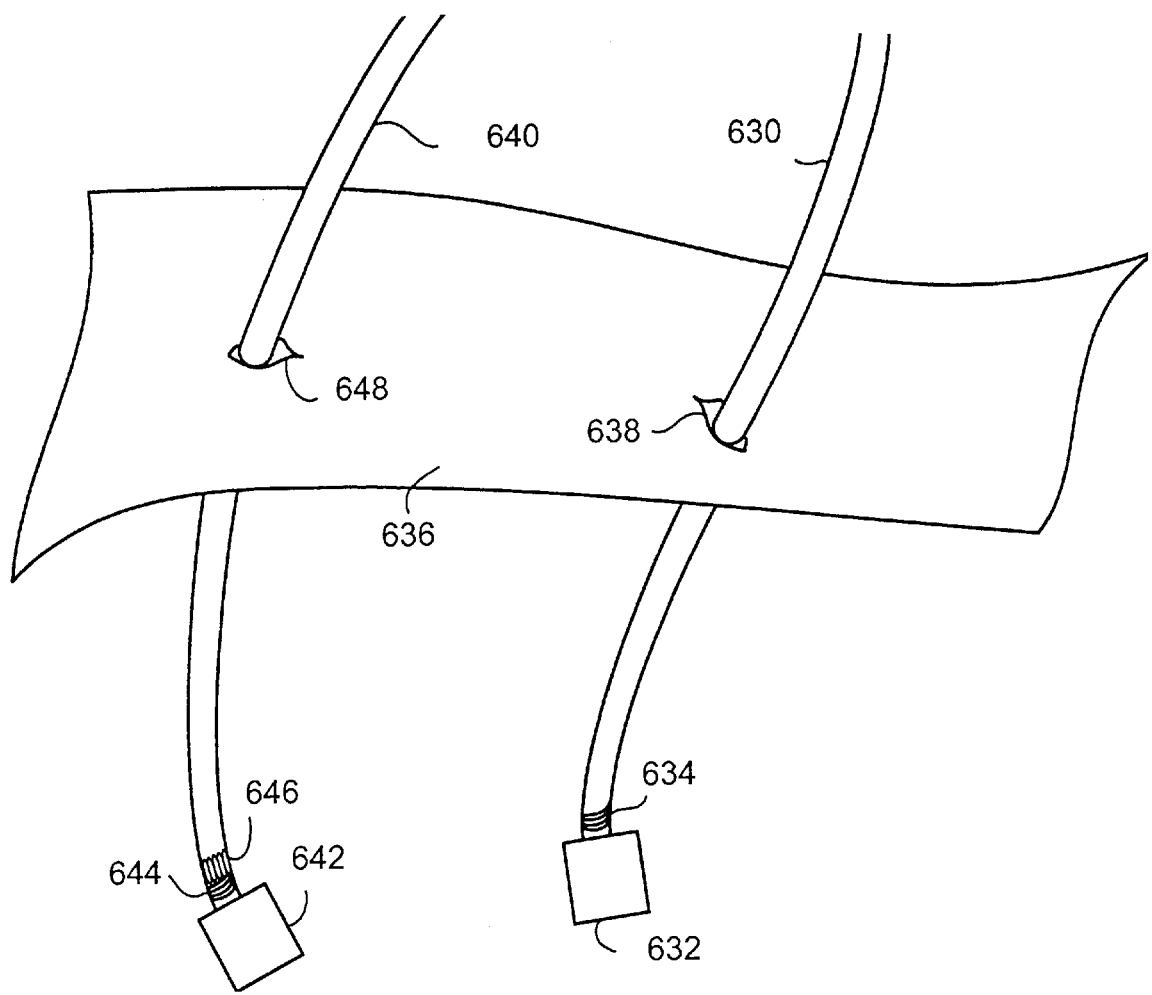
FIG. 14 is an illustration of two minimal invasive tools, constructed and operative in accordance with another preferred embodiment of the present invention.

In accordance with a further aspect of the invention, the position and orientation system of the invention is incorporated in laparoscopy devices and procedure Reference is now made to FIG. 14, which is an illustration of two minimal invasive tools, generally referenced 630 and 640, constructed and operative in accordance with another preferred embodiment of the invention.

Minimal invasive tool 630 is generally a guiding element, which is ended by a surgical tool, generally referenced 632. The surgical tool 632 can be any known device which is used in the process of minimal invasive surgery, such as a marking device, devices used for performing biopsies, surgical devices, laser cutting, treating and tissue welding devices and the like.

Minimal invasive tool 640 is generally similar to tool 630 and includes a surgical tool 642 and a pair of position and orientation sensors 644 and 646, where sensor 644is directed in the axial direction of tool 640 and sensor 646 is directed perpendicular thereto.

The minimal invasive tools 630 and 640 are inserted into the body of the patient through minimal size holes, 638 and 648, respectfully, in the skin layer 636. The use of such techniques reduces the trauma caused to the treated area. Conventional laparoscopy often requires that a camera and illumination means be inserted into the treated volume, since a simple line of sight is not available to the physician. In accordance with this aspect of the invention, no camera or illumination device have to be inserted into the treated volume. The position and orientation of the surgical tools are determined by the system of the invention and are indicated on an image of the treated volume, for the physician to see.

It will be appreciated by persons skilled in the art that the present invention is not limited to what has been particularly shown and described hereinabove Rather the scope of the present invention is defined only by the claims, which follow.

What is claimed is:

1. Apparatus for determining the position and orientation of a surgical tool relative to a reference frame, in association with an image, comprising:

a magnetic field transmitter, including at least one magnetic field generating element;

a detection probe including at least one magnetic field detector;

a signal generation module, connected to said at least one magnetic field generating element;

a detection processor, connected to said detection probe; and mounting means, for mounting onto said surgical tool, said signal generation module determining a multiple frequency transmit signal and providing said multiple frequency transmit signal to said magnetic field transmitter, said detection processor receiving a detected signal from said detection probe, at least a portion of said detected signal corresponding to said multiple frequency transmitted signal, determining the location and orientation of said detection probe from the power of said at least a portion of said detected signal and indicating the location of said surgical tool within said image.

2. The apparatus according to claim 1, wherein said detection probe includes at least three magnetic field detectors.

3. The apparatus according to claim 1, wherein the number of said at least one magnetic generating element is at least three.

4. The apparatus according to claim 1, wherein said signal generation module comprises an digital to analog converter and a signal processor connected thereto, said signal processor determining a digital transmit signal, said digital to analog converter converting said digital signal to a respective analog signal and providing said analog signal to said magnetic field transmitter.

5. The apparatus according to claim 4, wherein said digital signal includes at least one channel.

6. The apparatus according to claim 5, wherein each said at least one channel includes at least one frequency.

7. The apparatus according to claim 5, wherein each said at least one channel includes a plurality of frequencies and wherein said frequencies are transmitted in accordance with a predetermined sequence.

8. The apparatus according to claim 1, wherein said transmit signal channel includes at least one frequency.

9. The apparatus according to claim 1, wherein each said at least one channel includes at least three frequencies.

10. The apparatus according to claim 1, further comprising:

an ultrasound detector, connected to said detection processor, said ultrasound detector capturing a plurality of ultrasound frames; and an image location and orientation detector, mounted on said ultrasound detector, and connected to said detection processor, said image location and orientation detector detecting the location and orientation of each said ultrasound frames, wherein said detection processor constructs said image from said ultrasound frames and the detected location and orientation of each said frames with respect to the detected location and orientation of said surgical tool.

11. The apparatus according to claim 1, wherein said a detection probe is wirelessly connected to said detection processor.

12. A medial device comprising:

a housing a magnetic detection probe, for detecting a plurality of magnetic fields;

a biometric unit; and a controller, connected to said magnetic detection probe, said biometric unit and a storage unit, wherein said controller receives magnetic field detection information from said magnetic detection probe, wherein said controller operates said biometric unit in association with said magnetic field detection information.

13. The medial device according to claim 12, further comprising a transmitter connected to said controller for transmitting said magnetic field detection information.

14. The medial device according to claim 12, wherein said biometric unit includes at least one of the devices in the list consisting of:

an image detection unit;

a substance releasing unit; and a biometric sampling unit.

15. The medial device according to claim 12 further comprises a storage unit, connected to said controller, for storing said magnetic field detection information.

16. The medial device according to claim 15, wherein said biometric unit comprises a biomedical sensor, wherein said biometric unit provides said controller detected biometric information and wherein said controller produces a plurality of records, each said records including a portion of said biometric information and a respective portion of said detected magnetic field information.

17. The medial device according to claim 16 further comprising a storage unit, wherein said controller stores said records in said storage unit.

18. The medial device according to claim 16 further comprising a wireless transmitter, connected to said controller, wherein said controller provides said records to said wireless transmitter and wherein said transmitter transmits said records to an external receiver.

19. The medial device according to claim 12 wherein said plurality of magnetic fields are generated by an external transmitter.

20. The medial device according to claim 19 wherein said plurality of magnetic fields are generated by said external transmitter in accordance with a predetermined sequence.

21. The medial device according to claim 19 wherein said plurality of magnetic fields are generated by said external transmitter, continuously.

22. Method for calibrating a reference image onto a volume, from which the image is produced, the method comprising the steps of:

determining a plurality of locations in said volume, said locations being visible, said locations being present in said reference image;

detecting a magnetic field reading in each said locations; and calibrating said reference image with respect to said magnetic field readings, onto said volume.

23. The method according to claim 22, further comprising the steps of:

receiving additional magnetic field readings, each in an additional location within said volume; and determining the location and orientation of said additional location, within said reference frame.

24. Imaging system comprising:

an inner body ultrasound detector; and a location and orientation detector, located in proximity of said inner body ultrasound detector, wherein said inner body ultrasound detector detects a plurality of two-dimensional images, wherein said location and orientation detector detects the location and orientation of each said two-dimensional images.

25. The imaging system according to claim 24, further comprising a three dimensional image generator, connected to said inner body ultrasound detector and to said location and orientation detector, wherein said three dimensional image generator processes said two-dimensional images, each with its respecting location and orientation information, thereby producing a three dimensional image.

26. The imaging system according to claim 25, further comprising a storage unit connected between said three dimensional image generator and said inner body ultrasound detector and said location and orientation detector, for intermediately storing said two-dimensional images, each with its respecting location and orientation information.

27. The imaging system according to claim 25, further comprising a combining processor, connected to said three dimensional image and interfacing at least one additional location and orientation detector, wherein said combining processor receives additional location and orientation information from said at least one additional location and orientation detector, and wherein said combining processor produces an indication of said additional location and orientation information onto said three-dimensional image.

28. The imaging system according to claim 24, wherein said inner body ultrasound detector includes an angular ultrasound transceiver.

29. The imaging system according to claim 24, wherein said inner body ultrasound detector includes a radial ultrasound transceiver.

30. The imaging system according to claim 24, wherein said location and orientation detector includes at least one axial magnetic detector.

31. The imaging system according to claim 24, wherein said location and orientation detector detects magnetic field in at least one axial magnetic direction.

32. The imaging system according to claim 31, wherein said location and orientation detector detects magnetic field in at least one frequency in each said at least one axial magnetic direction.

33. The imaging system according to claim 24, wherein said location and orientation detector detects magnetic field in at least one frequency.

34. The imaging system according to claim 24, wherein said location and orientation detector is mounted on said inner body ultrasound detector.

35. The imaging system according to claim 24, wherein said inner body ultrasound detector is mounted on a catheter and wherein said location and orientation detector is mounted on the tip of said catheter, in the vicinity of said inner body ultrasound detector.

36. The imaging system according to claim 24, wherein said inner body ultrasound detector includes an inner vascular ultrasound transceiver.

37. The imaging system according to claim 24, further comprising a surgical tool location and orientation detector, to be mounted on a surgical tool, said surgical tool location and orientation detector detecting the location and orientation of said surgical tool, in the coordinate system of said location and orientation detector.

38. The imaging system according to claim 24, further comprising a processor, for reconstructing a three dimensional image from said two dimensional images, by placing said two dimensional images in a three dimensional volume, each according to its respective detected location and orientation.

39. The imaging system according to claim 38, further comprising a surgical tool location and orientation detector, to be mounted on a surgical tool, said surgical tool location and orientation detector detecting the location and orientation of said surgical tool, in the coordinate system of said location and orientation detector.

40. The imaging system according to claim 39, wherein said processor further adds a representation of said surgical tool onto said three dimensional volume, according to detected location and orientation of said surgical tool.

41. Method for producing a three dimensional image, comprising the steps of:

detecting a plurality of two-dimensional ultrasound images, from the inner section of a scanned volume;

detecting the location and orientation of a selected vector in each said two dimensional ultrasound images; and determining a three dimensional representation for each said two-dimensional images, according to the location and orientation thereof.

42. The method according to claim 41, further comprising the step of producing a three-dimensional image from said three-dimensional representations.

43. The method according to claim 42, further comprising the step of receiving additional location and orientation information and producing an indication thereof onto said three-dimensional image.

44. The method according to claim 43, further comprising the step of producing a visible representation of said three-dimensional image and said indication.

45. The method according to claim 41, further comprising the step of inserting an ultrasound detector into said inner section of said scanned volume.

46. The method according to claim 41, wherein said two-dimensional ultrasound images include angular two-dimensional ultrasound images.

47. The method according of claim 41, wherein said two-dimensional ultrasound images include angular two-dimensional ultrasound images.

* * * * *